(12) United States Patent
Chung et al.

(10) Patent No.: US 7,863,214 B2
(45) Date of Patent: Jan. 4, 2011

(54) CATALYSTS FOR POLYMERIZING CYCLIC OLEFIN

(75) Inventors: Young Keun Chung, Seoul (KR); Il Gu Jung, Chungcheongbuk-do (KR); Sung Ho Chun, Daejeon (KR); Young Whan Park, Yuseong-gu (KR); Sung Cheol Yoon, Daejeon (KR); TaeSun Lim, Daejeon (KR); Jungmin Lee, Daejeon (KR); Dai Seung Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 1127 days.

(21) Appl. No.: 11/542,166

(22) Filed: Oct. 4, 2006

(65) Prior Publication Data

US 2007/0093624 A1    Apr. 26, 2007

(30) Foreign Application Priority Data

Oct. 5, 2005 (KR) ............... 10-2005-0093530
Oct. 2, 2006 (KR) ............... 10-2006-0096848

(51) Int. Cl.
 *B01J 27/24* (2006.01)
(52) U.S. Cl. .................................. 502/200
(58) Field of Classification Search ............ 502/200
 See application file for complete search history.

(56) References Cited

U.S. PATENT DOCUMENTS 5,468,819 A * 11/1995 Goodall et al. ............ 526/171
5,728,839 A    3/1998 Herrmann et al.
6,455,650 B1 * 9/2002 Lipian et al. ............... 526/171
2005/0215735 A1   9/2005 Goodall et al.

FOREIGN PATENT DOCUMENTS

WO    WO 02/079126 A1    10/2002

OTHER PUBLICATIONS

Mcguinness et al., "Zerovalent Palladium and Nickel Complexes of Heterocyclic Carbenes: Oxidative Addition of Organic Halides, Carbon-Carbon Coupling Processes, and the Heck Reaction", Organometallics 1999, 18, pp. 1596-1605.

* cited by examiner

*Primary Examiner*—Ling-Siu Choi
*Assistant Examiner*—Sonya Wright
(74) *Attorney, Agent, or Firm*—McKenna Long & Aldridge LLP

(57) ABSTRACT

Provided is a metal catalyst complex for preparing a cyclic olefin-based polymer by addition polymerization of a cyclic olefin-based monomer, which is represented by Formula 1 below:

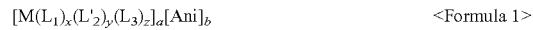

$[M(L_1)_x(L'_2)_y(L_3)_z]_a[Ani]_b$  <Formula 1> wherein M is a Group X metal; $[M(L_1)_x(L'_2)_y(L_3)_z]$ is a cationic precatalyst; $L_1$ is an anionic hydrocarbyl-containing ligand; $L'_2$ is a neutral ligand; $L_3$ is an N-heterocyclic carbene ligand; [Ani] is an anion capable of weakly coordinating with the metal M; x is 1 or 2; y is 0 to 4; z is 1 or 2; $2 \leq x+y+z \leq 6$; a and b are each 1 to 10.

The metal catalyst complex has an N-heterocyclic carbene ligand, and thus, is excellent in thermal stability and reactivity.

7 Claims, 1 Drawing Sheet

CATALYSTS FOR POLYMERIZING CYCLIC OLEFIN

CROSS-REFERENCE TO RELATED PATENT APPLICATION

This application claims priority from Korean Patent Application No. 10-2005-0093530 filed on Oct. 5, 2005, and No. 10-2006-0096848 filed on Oct. 2, 2006, in the Korean Intellectual Property Office, the disclosures of which are incorporated herein in their entireties by reference.

BACKGROUND OF THE INVENTION

1. Field of the Invention

The present invention relates to a metal catalyst complex for preparing an olefin-based polymer, a precatalyst for preparing the metal catalyst complex, a method of preparing the precatalyst, and a method of preparing the metal catalyst complex. More particularly, the present invention relates to a metal catalyst complex for preparing a cyclic olefin-based addition polymer, including an N-heterocyclic carbene (NHC) ligand, a precatalyst for preparing the metal catalyst complex, a method of preparing the precatalyst, and a method of preparing the metal catalyst complex.

2. Description of the Related Art

Cyclic olefin polymers, which are polymers composed of cyclic olefin monomers such as norbornene, have better transparency, heat resistance, and chemical resistance, and much lower birefringence and hygroscopicity, compared with conventional olefin-based polymers, and thus, can be widely applied as optical materials for CDs, DVDs, or POFs (Plastic Optical Fibers), information and electronic materials for capacitor films or low dielectrics, medical materials for low-absorbent syringes or blister packagings, etc. In particular, polynorbornenes are noncrystalline polymers which have a high glass transition temperature, a high refractive index, and a low dielectric constant, and thus, have been widely used as electronic materials. Much research about polynorbornenes has been actively done by Heitz et al [(a) T. F. A. Haselwander, W. Heitz, S. A. Krugel, J. H. Wendorff, *Macromolecules*, 1997, 30, 534. (b) T. F. A. Haselwander, W. Heitz, S. A. Krugel, J. H. Wendorff, *Macromol. Chem, Phys.* 1996, 197, 3435.].

Norbornene monomers can be easily polymerized since they can be easily converted to polymers in the presence of various palladium or nickel complexes and cocatalysts [Ni: (a) WO95 14048A1 (1995), B. F. Goodrich Co., invs.: B. L. Goodall, G. M. Benedikt, L. H. McIntosh III, D. A. Barnes; *Chem. Abstr.* 1995, 123, 341322p. (b) EP 445755 A2 (1991), Idemitsu Kosan Co. Ltd., invs.: H. Maezawa, J. Aiura, S. Asahi. *Chem. Abstr* 1991, 115, 256943g., Pd: (a) U.S. Pat. No. 3,330,815 (1967), Union Carbide Corp., invs.: J. E. McKeon, P. S. Starcher; *Chem. Abstr.* 1967, 67, 64884g. (b) F. Hojabri, M. M. Mohaddes, A. Talab, *Polymer* 1976, 17, 710].

However, norbornene monomers having a saturated hydrocarbon ring structure are hardly soluble in organic solvents, and are inferior in adsorptivity to metals, etc. which is required for use of them as electronic materials, thereby limiting the applications of the norbornene monomers. In view of these problems, extensive research has been actively conducted. In order to easily change the physical properties of polymers, for example, to improve the solubility of conventional polynorbornenes, and to provide new physical properties to the polynorbornenes, a method of modifying the chemical structures of norbornene monomers and a method of incorporating new functional groups to norbornene monomers have been proposed. In particular, low solubility in organic solvents of norbornene monomers can be easily overcome by incorporating polar functional groups to the norbornene monomers. Alternatively, research about norborene/ethane copolymerization [(a) H. Cherdron, M. J. Brekner, F. Osan, *Angew. Makromol. Chem.* 1994, 223, 121. (b) M. Arndt, I. Beulich, *Macromol. Chem. Phys.* 1998, 199, 1221] or norbornene/functionalized norbornene copolymerization [T. F. A. Haselwander, W. Heitz, M. Maskos, *Macromol, Rapid. Commun.* 1997, 198, 3963] has been actively conducted. These copolymerization reactions can also contribute to better adsorption of copolymers with other objects.

A catalyst mainly used in the preparation of cyclic olefin polymers was a catalyst complex including, as a cocatalyst, an organic phosphine compound that has been used as a σ electron donor ligand. For example, U.S. Pat. No. 6,455,650 discloses a method of polymerizing a functionalized norbornene-based monomer in the presence of a catalyst complex represented by $[(R')_zM(L')_x(L'')_y]_b[WCA]_d$ where phosphine and a hydrocarbyl (e.g., allyl)-containing hydrocarbon are used as ligands. Sen, et al. [Organometallics 2001, Vol. 20, 2802-2812] reported ester norbornene polymerization catalyzed by $[(1,5-cyclooctadiene)(CH_3)Pd(Cl)]$ and cocatalyzed by phosphine ($PPh_3$) and $[Na]^+[B(3,5-(CF_3)_2C_6H_3)_4]^-$.

However, separate addition of a phosphine cocatalyst requires a separate step for converting a catalyst precursor to an activated catalyst and significantly reduces catalyst activity in the presence of a polar functional group-containing cyclic olefin monomer.

Recently, preparation of polar functional group-containing norbornene polymers in the presence of phosphonium compounds as cocatalysts have been disclosed in Korean Patent Laid-Open Publication Nos. 2004-0052612 and 2004-0074307.

For synthesis of an aromatic olefin monomer (e.g.: stilbene), EP 0721953B1 discloses a metal catalyst complex including an N-heterocyclic carbene (NHC) ligand instead of a phosphine ligand. However, the working examples of this patent document disclose that the NHC ligand is mainly substituted simply by an alkyl group or a sulfonated alkyl group.

As one of various methods for improving the performance of metal catalysts, a method of partially substituting ligands with various functional groups has been proposed. The method is considering an electronic effect of a ligand. The improvement of the performance of catalysts through adjustment of the electronic effect of a ligand has been reported in several documents. For example, an improvement of catalyst activity through a ligand electronic effect adjusted by changing a substituent of a Grubbs ruthenium carbene catalyst ligand has been reported [(a) Trnka, T. M.; Grubbs, R. H. Acc. Chem. Res. 2001, 34, 18-29. (b) Love, J. A.; Sanford, M. S.; Day, M. W.; Grubbs, R. H. J. Am. Chem. Soc. 2003, 125, 10103-10109].

With respect to catalysts used in polymer synthesis, Waymouth has found that a ligand electronic effect plays an important role in adjusting the stereoselectivity of propylene polymerization in the presence of a zirconocene catalyst [Lin, S.; Hauptman, E.; Lal, T. K.; Waymouth, R. M.; Quan, R. W.; Ernst, A. B. J. Mol. Catal. A: Chem. 1998, 136, 23-33]. Coates has reported that when carbon dioxide ($CO_2$) and epoxide are copolymerized in the presence of a β-diiminate zinc alkoxide catalyst, partial substitution of a ligand with a cyano group enables to significantly increase a polymerization rate [Moore, D. R.; Cheng, M.; Lobkovsky, E. B.; Coates, G. W. Angew. Chem., Int. Ed. 2002, 41, 2599-2602].

However, until now, there was no report about a further improvement in performance of metal catalysts through a ligand electronic effect achieved by partially substituting a NHC ligand with various functional groups affecting ligand electron density. Therefore, it is necessary to prepare a new metal catalyst complex which shows better performance by substituting a NHC ligand with various functional groups.

SUMMARY OF THE INVENTION

The present invention provides a metal catalyst complex which is newly structured for preparing a cyclic olefin polymer.

The present invention also provides a precatalyst for preparing the metal catalyst complex.

The present invention also provides a method of preparing the precatalyst.

The present invention also provides a method of preparing a metal catalyst complex using the precatalyst.

According to an aspect of the present invention, there is provided a metal catalyst complex for preparing a cyclic olefin-based polymer by addition polymerization of a cyclic olefin-based monomer, which is represented by Formula 1 below:

$$[M(L_1)_x(L'_2)_y(L_3)_z]_a[Ani]_b \qquad \text{<Formula 1>}$$

wherein M is a Group X metal, $[M(L_1)_x(L'_2)_y(L_3)_z]$ is a cationic complex, $L_1$ is an anionic hydrocarbyl-containing ligand, $L'_2$ is a neutral ligand, $L_3$ is an N-heterocyclic carbene ligand,

[Ani] is an anion capable of weakly coordinating with the metal M, x is 1 or 2; y is 0 to 4; z is 1 or 2; $2 \leq x+y+z \leq 6$, a and b are respectively the number of cations and the number of anions capable of weakly coordinating with the metal M and are each a number of 1-10 which is used to satisfy the net charge balance of the metal catalyst complex, wherein for each of $L_1$, $L'_2$, and $L_3$, when a plurality of ligands are present in a molecule of the metal catalyst complex, the ligands may be the same or different.

According to an embodiment of the metal catalyst complex of the present invention, the cyclic olefin-based monomer may be a compound represented by Formula 2 below:

<Formula 2> wherein m is an integer of 0 to 4, $R_7$, $R'_7$, $R''_7$, and $R'''_7$ are each independently a polar functional group or a nonpolar functional group, and $R_7$, $R'_7$, $R''_7$, and $R'''_7$ may be connected to form a C4-C12 saturated or unsaturated cyclic group or a C6-C24 aromatic ring, wherein the nonpolar functional group is selected from the group consisting of hydrogen; halogen; C1-C20 straight or branched alkyl, haloalkyl, alkenyl, or haloalkenyl; C3-C20 straight or branched alkynyl or haloalkynyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; and C7-C15 aralkyl which is unsubstituted or substituted by alkyl, alkenyl, alkynyl, halogen, haloalkyl, haloalkenyl, or haloalkynyl, but is not limited to the illustrated examples, and wherein the polar functional group is a non-hydrocarbonaceous polar group including at least one of oxygen, nitrogen, phosphorus, sulfur, silicon, and boron, and is selected from the group consisting of:

—$R^8OR^9$, —$OR^9$, —$OC(O)OR^9$, —$R^8OC(O)OR^9$, —$C(O)R^9$, —$R^8C(O)R^9$, —$OC(O)R^9$, —$R^8C(O)OR^9$, —$C(O)OR^9$, —$R^8OC(O)R^9$, —$(R^8O)_k$—$OR^9$, —$(OR^8)_k$—$OR^9$, —$C(O)$—$O$—$C(O)R^9$, —$R^8C(O)$—$O$—$C(O)R^9$, —$SR^9$, —$R^8SR^9$, —$SSR^8$, —$R^8SSR^9$, —$S(=O)R^9$, —$R^8S(=O)R^9$, —$R^8C(=S)R^9$, —$R^8C(=S)SR^9$, —$R^8SO_3R^9$, —$SO_3R^9$, —$R^8N=C=S$, —$N=C=S$, —$NCO$, $R^8$—$NCO$, —$CN$, —$R^8CN$, —$NNC(=S)R^9$, —$R^8NNC(=S)R^9$, —$NO_2$, —$R^8NO_2$, —$P(R^9)_2$, —$R^8P(R^9)_2$, —$P(=O)(R^9)_2$, —$R^8P(=O)(R^9)_2$,

[chemical structure diagrams of various functional groups containing $R^{11}$, $R^{12}$, $R^{13}$, $R^{14}$ substituents with C(O)N, OC(O)N, SR, OSR, OSOR, B, N—C, P, Si, and related moieties]

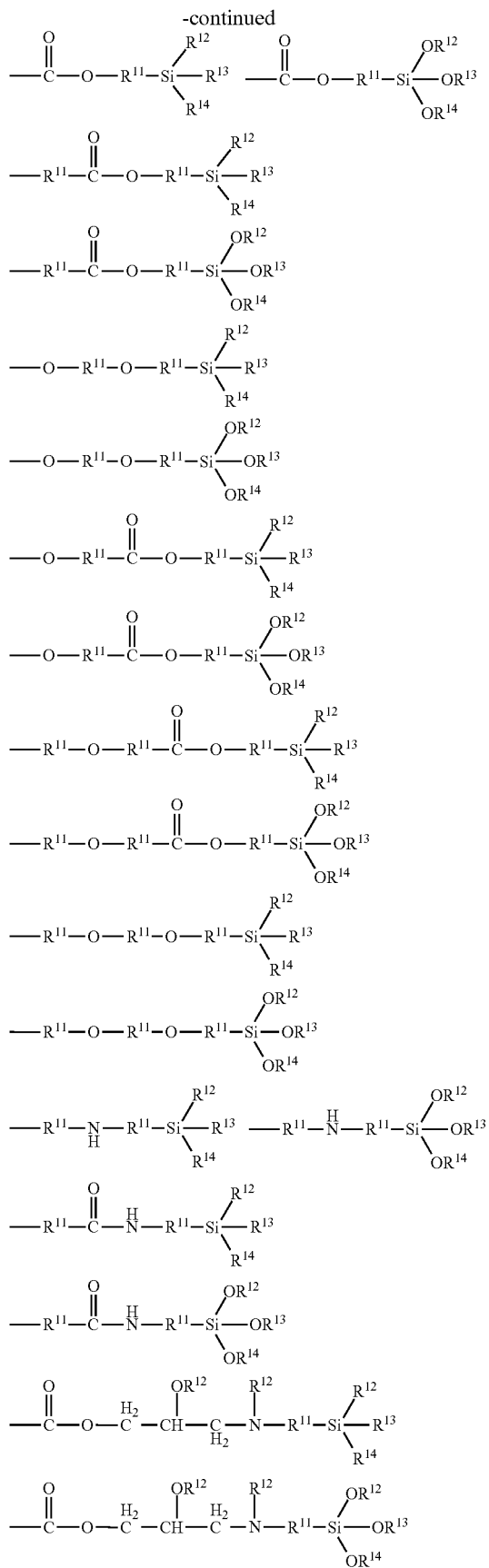
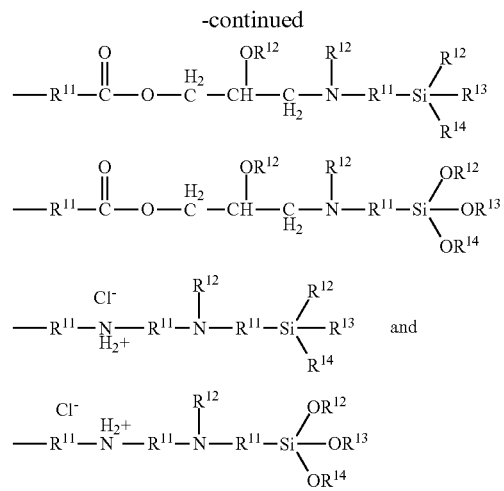

but is not limited to the illustrated examples.

In the polar functional group, $R^8$'s and $R^{11}$'s are each C1-C20 straight or branched alkylene, haloalkylene, alkenylene, or haloalkenylene; C3-C20 straight or branched alkynylene or haloalkynylene; C3-C12 cycloalkylene which is unsubstituted or substituted by alkyl, alkenyl, alkynyl, halogen, haloalkyl, haloalkenyl, or haloalkynyl; C6-C40 arylene which is unsubstituted or substituted by alkyl, alkenyl, alkynyl, halogen, haloalkyl, haloalkenyl, or haloalkynyl; or C7-C15 aralkylene which is unsubstituted or substituted by alkyl, alkenyl, alkynyl, halogen, haloalkyl, haloalkenyl, or haloalkynyl, $R^9$'s, $R^{12}$'s, $R^{13}$'s, and $R^{14}$'s are each hydrogen; halogen; C1-C20 straight or branched alkyl, haloalkyl, alkenyl, or haloalkenyl; C3-C20 straight or branched alkynyl or haloalkynyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or alkoxy, haloalkoxy, silyl, siloxy, aryloxy, haloaryloxy, carbonyloxy, or halocarbonyloxy, and k's are each an integer of 1 to 10.

According to another embodiment of the metal catalyst complex of the present invention, the N-heterocyclic carbene ligand may be at least one selected from the group consisting of compounds represented by Formulae 3A through 3D below:

<Formula 3A>

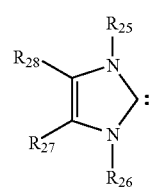

-continued

<Formula 3B>

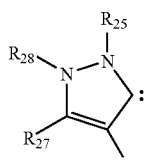

<Formula 3C>

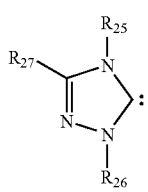

<Formula 3D>

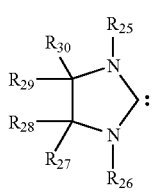

wherein $R_{25}$, $R_{26}$, $R_{27}$, $R_{28}$, $R_{29}$, and $R_{30}$ are each independently hydrogen, C1-C20 straight or branched alkyl, C3-C12 cycloalkyl, C2-C20 straight or branched alkenyl, C6-C15 cycloalkenyl, C6-C30 aryl, C6-C30 heteroatom-containing aryl, or C7-C30 aralkyl, which may be optionally substituted by at least one hydrocarbyl and/or heteroatom substituent selected from C1-C5 straight or branched alkyl, C1-C5 straight or branched haloalkyl, C2-C5 straight or branched alkenyl, C2-C5 straight or branched haloalkenyl, halogen, sulfur, oxygen, nitrogen, phosphorus, and a phenyl group. Here, the phenyl group may be optionally substituted by C1-C5 straight or branched alkyl, C1-C5 straight or branched haloalkyl, halogen, or a heteroatom, but is not limited to the illustrated examples, and the alkenyl may include allyl or vinyl.

According to another embodiment of the metal catalyst complex of the present invention, the [Ani] is an anion capable of weakly coordinating with the Group X metal M, and may be one selected from the group consisting of borate, aluminate, [SbF$_6$]—, [PF$_6$]—, [AsF$_6$]—, perfluoroacetate [CF$_3$CO$_2$]—, perfluoropropionate [C$_2$F$_5$CO$_2$]—, perfluorobutyrate [CF$_3$CF$_2$CF$_2$CO$_2$]—, perchlorate [ClO$_4$]—, p-toluenesulfonate [p-CH$_3$C$_6$H$_4$SO$_3$]—, [SO$_3$CF$_3$]—, boratabenzene, and carborane which is unsubstituted or substituted by halogen.

According to another embodiment of the metal catalyst complex of the present invention, the borate or the aluminate may be an anion represented by Formula 4A or 4B below:

[M'(R$_{30}$)$_4$]  <Formula 4A>

[M'(OR$_{30}$)$_4$]  <Formula 4B> wherein M' is boron or aluminum, and $R_{30}$'s are each independently halogen; C1-C20 straight or branched alkyl or alkenyl which is unsubstituted or substituted by halogen; C3-C12 cycloalkyl which is unsubstituted or substituted by halogen; C6-C40 aryl which is unsubstituted or substituted by halogen; C6-C40 aryl which is substituted by C3-C20 straight or branched trialkylsiloxy or C18-C48 straight or branched triarylsiloxy; or C7-C15 aralkyl which is unsubstituted or substituted by halogen or hydrocarbon.

According to another embodiment of the metal catalyst complex of the present invention, the metal catalyst complex may be represented by Formula 5 below:

<Formula 5>

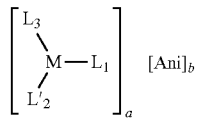

wherein M, $L_1$, $L'_2$, $L_3$, [Ani], a, and b are as defined above.

According to another embodiment of the metal catalyst complex of the present invention, the metal catalyst complex may be one selected from the group consisting of compounds represented by Formulae 6A through 6D below:

<Formula 6A>

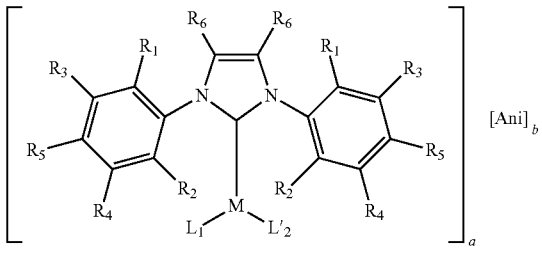

<Formula 6B>

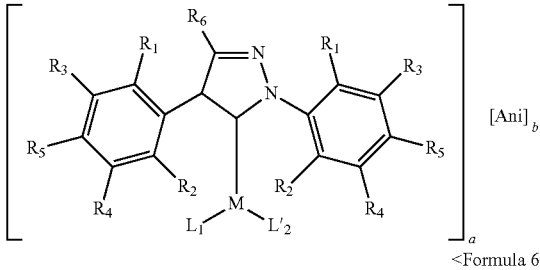

<Formula 6C>

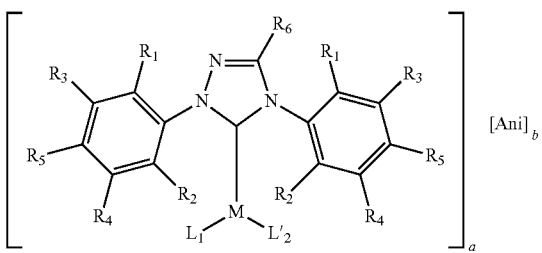

<Formula 6D>

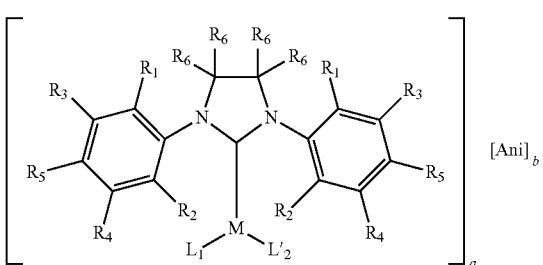

wherein M, $L_1$, $L'_2$, [Ani], a, and b are as defined above, and $R_1$ through $R_6$ are each independently hydrogen; halogen; C1-C20 straight or branched alkyl, alkoxy, or alkenyl;

C5-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or C3-C20 alkynyl, but are not limited to the illustrated examples. Here, the alkenyl may include allyl or vinyl.

At least one of $R_1$ to $R_6$ is halogen or halogen-containing alkyl, aryl, aralkyl, or alkylaryl group.

According to another embodiment of the metal catalyst complex of the present invention, the metal catalyst complex may be represented by Formula 7 below:

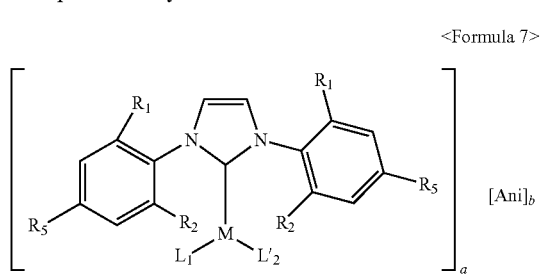

<Formula 7> wherein M, $L_1$, $L'_2$, [Ani], $R_1$, $R_2$, $R_5$, a, and b are as defined above, and at least one of $R_1$, $R_2$, and $R_5$ is halogen or a halogen-containing alkyl, aryl, aralkyl, or alkylaryl group when the metal catalyst complex is used in preparation methods of the present invention.

According to another embodiment of the metal catalyst complex of the present invention, the metal catalyst complex may be represented by Formula 8 below:

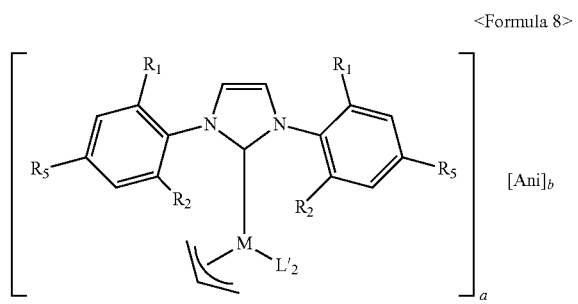

<Formula 8> wherein M, $L'_2$, [Ani], $R_1$, $R_2$, $R_5$, a, and b are as defined above,

is C3 allyl, and at least one of $R_1$, $R_2$, and $R_5$ is halogen or a halogen-containing alkyl, aryl, aralkyl, or alkylaryl group.

According to another aspect of the present invention, there is provided a precatalyst for preparing a metal catalyst complex for preparing a cyclic olefin-based polymer, which is represented by Formula 9 below:

$$M(L_1)_x(L_2)_y(L_3)_z$$ <Formula 9> wherein M, $L_1$, and $L_3$ are as defined above, $L_2$ is an anionic ligand selected from a hydrogen anion, a halogen anion, an alkoxy anion (R"O—), a carboxylate anion (R"C(O)O—), R"C(O)S—, R"C(S)O—, R"$_2$N—, and R"$_2$P— where R" is the same as $L_1$, x is 0 or 2, z is 1 or 2, and $2 \leq x+y+z \leq 6$, wherein for each of $L_1$, $L_2$, and $L_3$, when a plurality of ligands are present in a molecule of the precatalyst, the ligands may be the same or different.

According to an embodiment of the precatalyst of the present invention, the precatalyst may be represented by Formula 9A below:

<Formula 9A> wherein M, $L_1$, $L_2$, and $L_3$ are as defined above.

According to another embodiment of the precatalyst of the present invention, the precatalyst may be one selected from compounds represented by Formulae 10A through 10D below:

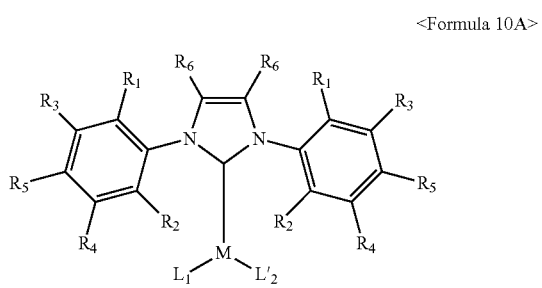

<Formula 10A>

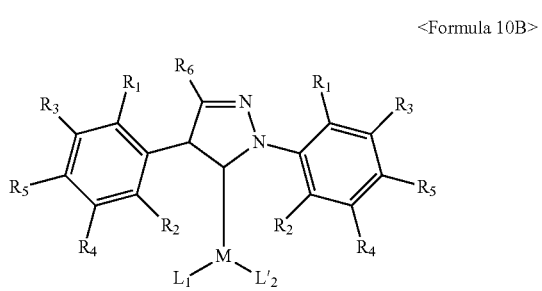

<Formula 10B>

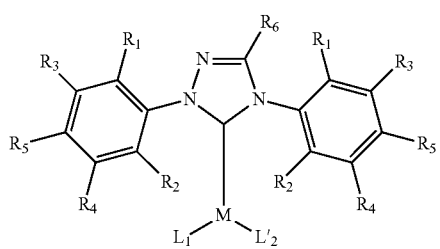

<Formula 10C>

-continued

<Formula 10D>

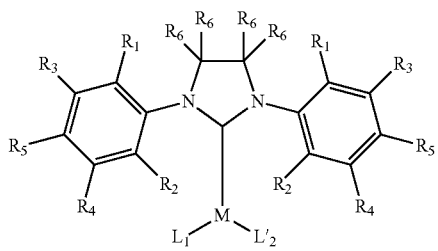

wherein M, $L_1$, $L_2$, $R_1$ through $R_6$ are as defined above, and at least one of $R_1$ through $R_6$ is halogen or a halogen-containing alkyl, aryl, aralkyl, or alkylaryl group.

According to another embodiment of the precatalyst of the present invention, the precatalyst may be represented by Formula 11 below:

<Formula 11>

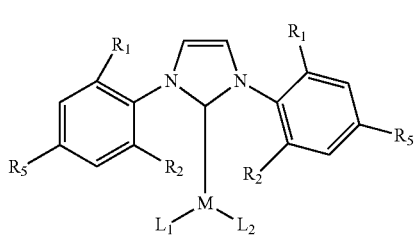

wherein M, $L_1$, $L_2$, $R_1$, $R_2$, and $R_5$ are as defined above, and at least one of $R_1$, $R_2$, and $R_5$ is halogen or a halogen-containing alkyl, aryl, aralkyl, or alkylaryl group.

According to another embodiment of the precatalyst of the present invention, the precatalyst may be represented by Formula 12 below:

<Formula 12>

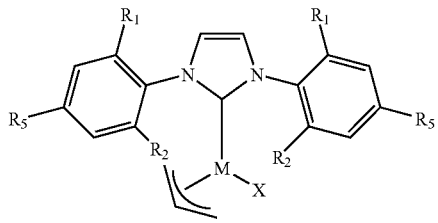

wherein M, $R_1$, $R_2$, and $R_5$ are as defined above,

is C3 allyl,
X is halogen, and
at least one of $R_1$, $R_2$, and $R_5$ is halogen or a halogen-containing alkyl, aryl, aralkyl, or alkylaryl group.

According to another aspect of the present invention, there is provided a method of preparing a precatalyst, the method including:

preparing a diimine compound represented by Formula 14 below by reacting an amine compound represented by Formula 13 below with glyoxal;

preparing an imidazolium salt represented by Formula 15 below by reacting the diimine compound with aldehyde in an acid condition;

preparing free carbene represented by Formula 16 below by reacting the imidazolium salt with an alkoxide compound; and preparing a precatalyst represented by Formula 12 above by reacting the free carbene with a Group X metal compound:

<Formula 13>

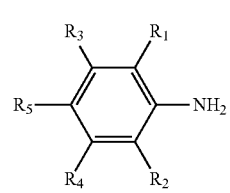

<Formula 14>

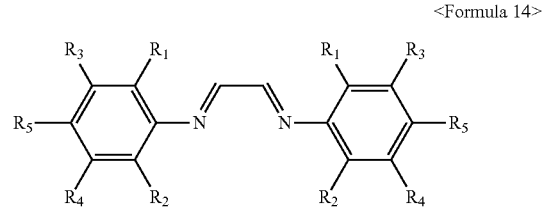

<Formula 15>

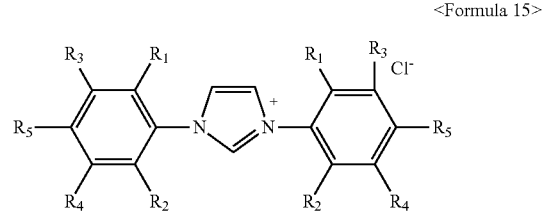

<Formula 16>

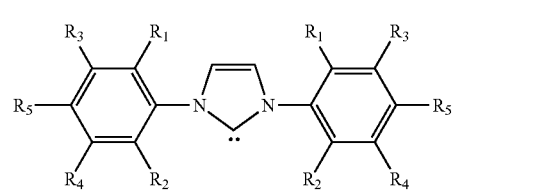

wherein $R_1$ through $R_5$ are as defined above.

According to another aspect of the present invention, there is provided a method of preparing a metal catalyst complex for preparing a cyclic olefin-based polymer by addition polymerization of a cyclic olefin-based monomer, the method including contacting the above-described precatalyst with a salt compound represented by Formula 17 below:

$[Cat]_a[Ani]_b$  <Formula 17> wherein a and b are each 1 to 10,

[Cat] is a cation selected from the group consisting of a hydrogen ion ($H^+$), an alkaline metal cation, a transition metal cation, and a cation-containing functional group, and

[Ani] is an anion capable of weakly coordinating with the metal M of the precatalyst and is as defined above.

In the method of preparing the metal catalyst complex, the precatalyst and the salt compound may be dissolved in an organic solvent selected from the group consisting of dichloromethane, dichloroethane, toluene, chlorobenzene, and a mixture thereof.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
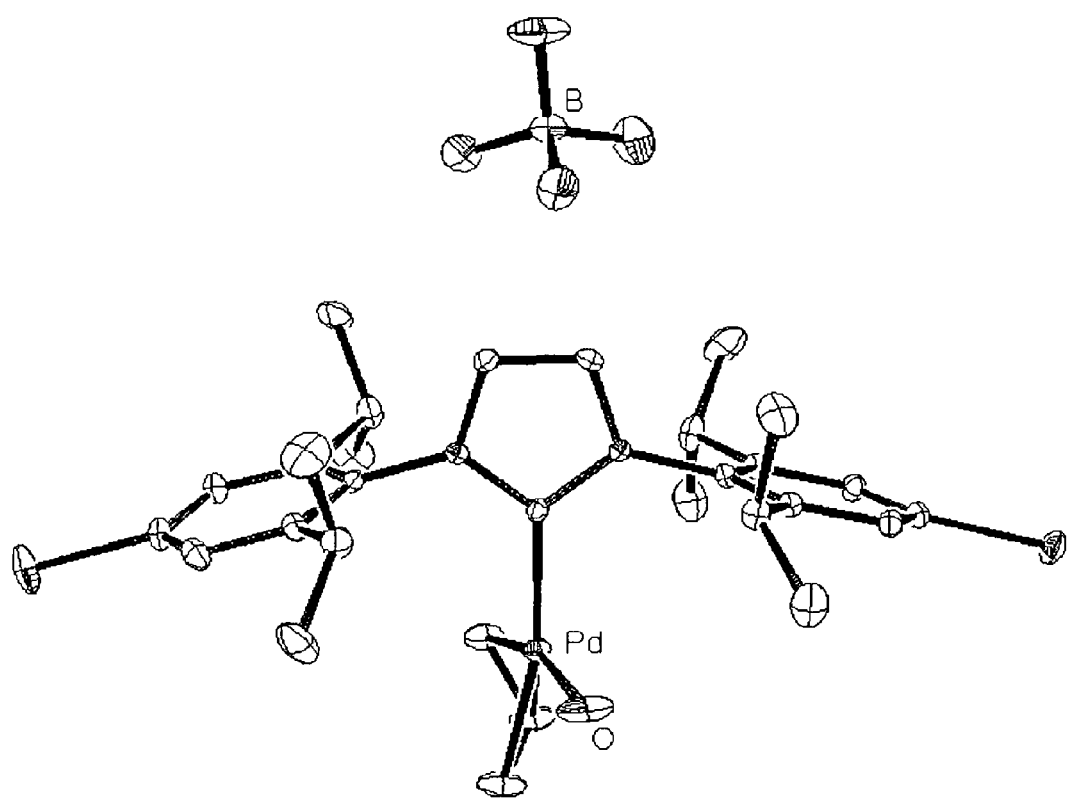
FIG. 1 is an X-ray crystallographic structure of a metal catalyst complex prepared in Example 10.

The present invention will now be described in more detail.

The present invention provides a metal catalyst complex for preparing a cyclic olefin polymer, which includes an N-heterocyclic carbene (NHC) ligand.

The metal catalyst complex for cyclic olefin polymerization according to the present invention is excellent in thermal stability and reactivity due to the presence of the NHC ligand, unlike conventional catalysts including a phosphine ligand.

Generally, NHC is a representative singlet carbene having one of structures represented by Formulae 3A through 3D below:

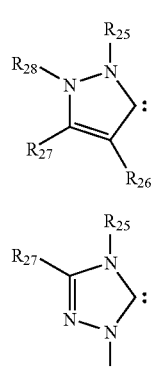
<Formula 3A>

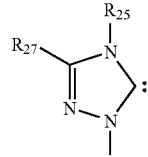
<Formula 3B>

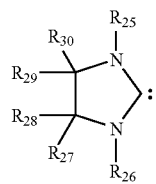
<Formula 3C>

<Formula 3D>

Metal complexes with NHC were first reported by Ofele in 1968 [K. Ofele, *J. Organomet. Chem.* 1968, 12, 42]. In 1986, Wanzilick first separated NHC and determined the crystal structure of NHC. As the structure and electron properties of NHC are disclosed, much research about NHC has been conducted. NHC is known to be a ligand which can serve as a better sigma donor than an organophosphine compound well known as a sigma donor ligand and can strongly bind with metals due to a little back-bonding property. Based on such unique characteristics of NHC, various transition metal complexes have been synthesized. Since 1990s, NHC has been widely applied as a catalyst for various organic reactions, a ligand for inorganic chemistry, or a building block of supramolecules [W. A. Herrmann *Angew. Chem. Int. Ed.* 2002, 41, 1290].

With respect to catalysts for cyclic olefin polymerization, conventionally, it is known that the use of a phosphine cocatalyst can significantly increase catalyst activity. Recently, however, it has been reported that NHC can serve as a phosphine surrogate, thereby forming active catalyst species [Hermann, W. A. Angew. Chem. Int. Ed. Engl. 1997, 36, 2163; Schroll, M., Trnka, T. M., Morgan, J. P. Grubbs, R. H. Tetrahedron Lett. 1999 40, 2247].

However, the application of NHC in a catalyst for addition polymerization of a cyclic olefin polymer has not yet been reported. In the metal catalyst complex for cyclic olefin polymerization according to the present invention, it is possible to adjust the electrophilicity of a center metal and the size of a catalytic active site by modifying the structure of NHC. In particular, in norbornene addition polymerization, a very bulky monomer must reach a catalytic active site. A solution to this problem can be accessed by using a catalyst having a different structure from a conventional catalyst. In this respect, the present inventors have prepared a new precatalyst (catalyst precursor) for cyclic olefin polymerization, having a novel structure by introducing a NHC ligand to a central metal which acts as a catalytic active site, without adding phosphine as a separate cocatalyst. The NHC ligand does the role of phosphine and controls the electronic and stereoscopic effect of the central metal.

The present invention provides a metal catalyst complex for preparing a cyclic olefin-based polymer by addition polymerization of a cyclic olefin-based monomer, which is represented by Formula 1 below:

$$[M(L_1)_x(L'_2)_y(L_3)_z]_a[Ani]_b \qquad <\text{Formula 1}>$$

wherein M is a Group X metal, $[M(L_1)_x(L'_2)_y(L_3)_z]$ is a cationic complex, $L_1$ is an anionic hydrocarbyl-containing ligand, $L'_2$ is a neutral ligand, $L_3$ is an N-heterocyclic carbene ligand,

[Ani] is an anion capable of weakly coordinating with the metal M, x is 1 or 2; y is 0 to 4; z is 1 or 2; $2 \leq x+y+z \leq 6$, a and b are respectively the number of cations and the number of anions capable of weakly coordinating with the metal M and are each a number of 1-10 which is used to satisfy the net charge balance of the metal catalyst complex, wherein for each of $L_1$, $L'_2$, and $L_3$, when a plurality of ligands are present in a molecule of the metal catalyst complex, the ligands may be the same or different.

In Formula 1 above, M may be any Group X metal. However, nickel or palladium is preferred.

In Formula 1 above, $L_1$ is an anionic hydrocarbyl-containing ligand. The anionic hydrocarbyl-containing ligand is any hydrocarbyl ligand which when removed from the center metal M, has a negative charge in its closed shell electron configuration, and may be selected from a hydrogen ligand, a C1-C20 straight or branched alkyl ligand, a C5-C10 cycloalkyl ligand, a C2-C20 straight or branched alkenyl ligand, a C6-C15 cycloalkenyl ligand, an allyl ligand, or a normal form thereof; a C6-30 aryl ligand; a C6-C30 heteroatom-containing aryl ligand; and a C7-C30 aralkyl ligand which may be optionally substituted by a hydrocarbyl and/or heteroatom substituent selected from C1-C5 straight or branched alkyl, C1-C5 straight or branched haloalkyl, C2-C5 straight or branched alkenyl, C2-C5 straight or branched haloalkenyl, halogen, sulfur, oxygen, nitrogen, phosphorus, and a phenyl group. Here, the phenyl group may be optionally substituted by C1-C5 straight or branched alkyl, C1-C5 straight or branched haloalkyl, halogen, or a heteroatom, but is not limited to the illustrated examples, and the alkenyl may include vinyl.

The anionic hydrocarbyl-containing ligand may also be selected from ligands represented by R'C(O)O, R'C(O)CHC(O)R', R'C(O)S, R'C(S)O, R'C(S)S, R'O, and (R')$_2$N where R' is the same as the above-defined L$_1$.

The cycloalkyl ligand and the cycloalkenyl ligand may be monocyclic or polycyclic ligands, the aryl ligand may be a monocyclic ligand (e.g., phenyl) or a fused ring (e.g., naphthyl). Any cycloalkyl group, any cycloalkenyl group, and any aryl group may also be connected to form a fused ring.

In Formula 1 above, L$_2$ is a neutral ligand, and may include a reactive diluent, a reactive monomer, DMF, DMSO, C4-C10 aliphatic diene, C4-C10 cyclic aliphatic diene, more specifically, butadiene, 1,6-hexadiene, cyclooctadiene, etc. Water, chloroalkane, alcohol, ether, ketone, nitrile, arene, phosphine oxide, organic carbonate or ester, or the like is also preferred.

The cyclic olefin-based monomer may be a compound represented by Formula 2 below:

<Formula 2>

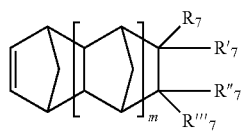

wherein m is an integer of 0 to 4,

R$_7$, R'$_7$, R"$_7$, and R'"$_7$ are each independently a polar functional group or a nonpolar functional group, and R$_7$, R'$_7$, R"$_7$, and R'"$_7$ may be connected to form a C4-C12 saturated or unsaturated cyclic group or a C6-C24 aromatic ring.

The nonpolar functional group may be selected from the group consisting of hydrogen; halogen; C1-C20 straight or branched alkyl, haloalkyl, alkenyl, or haloalkenyl; C3-C20 straight or branched alkynyl or haloalkynyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; and C7-C15 aralkyl which is unsubstituted or substituted by alkyl, alkenyl, alkynyl, halogen, haloalkyl, haloalkenyl, or haloalkynyl, but is not limited to the illustrated examples.

The polar functional group is a non-hydrocarbonaceous polar group including at least one of oxygen, nitrogen, phosphorus, sulfur, silicon, and boron, and may be selected from the group consisting of:

—R$^8$OR$^9$, —OR$^9$, —OC(O)OR$^9$, —R$^8$OC(O)OR$^9$, —C(O)R$^9$, —R$^8$C(O)R$^9$, —OC(O)R$^9$, —R$^8$C(O)OR$^9$, —C(O)OR$^9$, —R$^8$OC(O)R$^9$, —(R$^8$O)$_k$—OR$^9$, —(OR$^8$)$_k$—OR$^9$, —C(O)—O—C(O)R$^9$, —R$^8$C(O)—O—C(O)R$^9$, —SR$^9$, —R$^8$SR$^9$, —SSR$^8$, —R$^8$SSR$^9$, —S(=O)R$^9$, —R$^8$S(=O)R$^9$, —R$^8$C(=S)R$^9$, —R$^8$C(=S)SR$^9$, —R$^8$SO$_3$R$^9$, —SO$_3$R$^9$, —R$^8$N=C=S, —N=C=S, —NCO, R$^8$—NCO, —CN, —R$^8$CN, —NNC(=S)R$^9$, —R$^8$NNC(=S)R$^9$, —NO$_2$, —R$^8$NO$_2$, —P(R$^9$)$_2$, —R$^8$P(R$^9$)$_2$, —P(=O)(R$^9$)$_2$, —R$^8$P(=O)(R$^9$)$_2$,

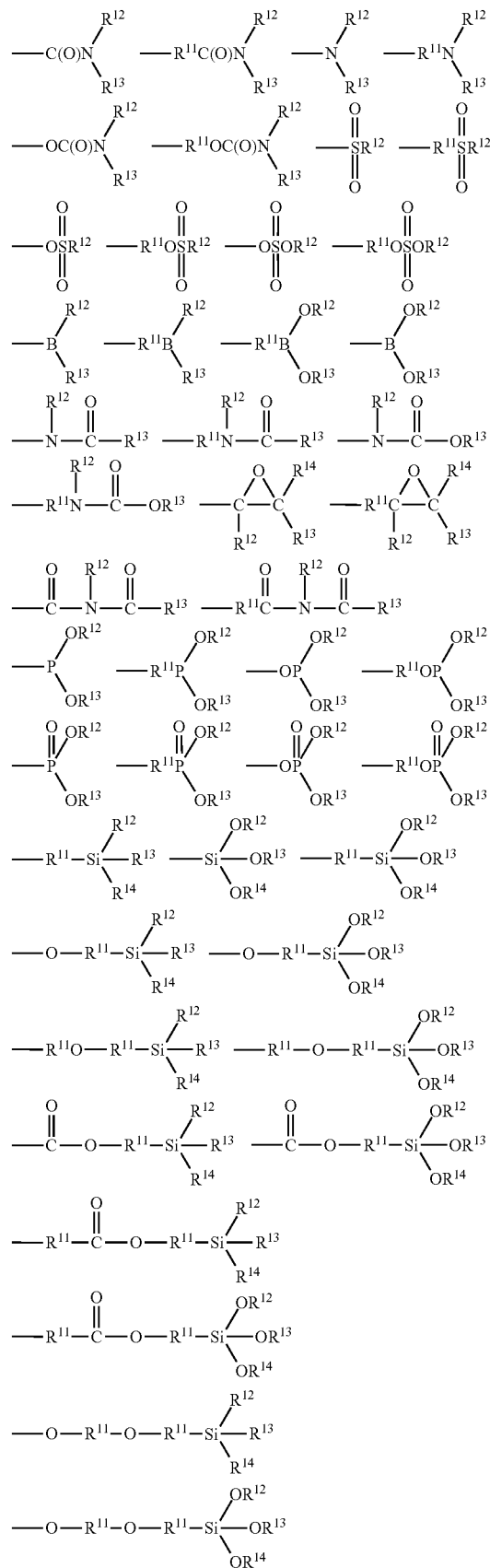

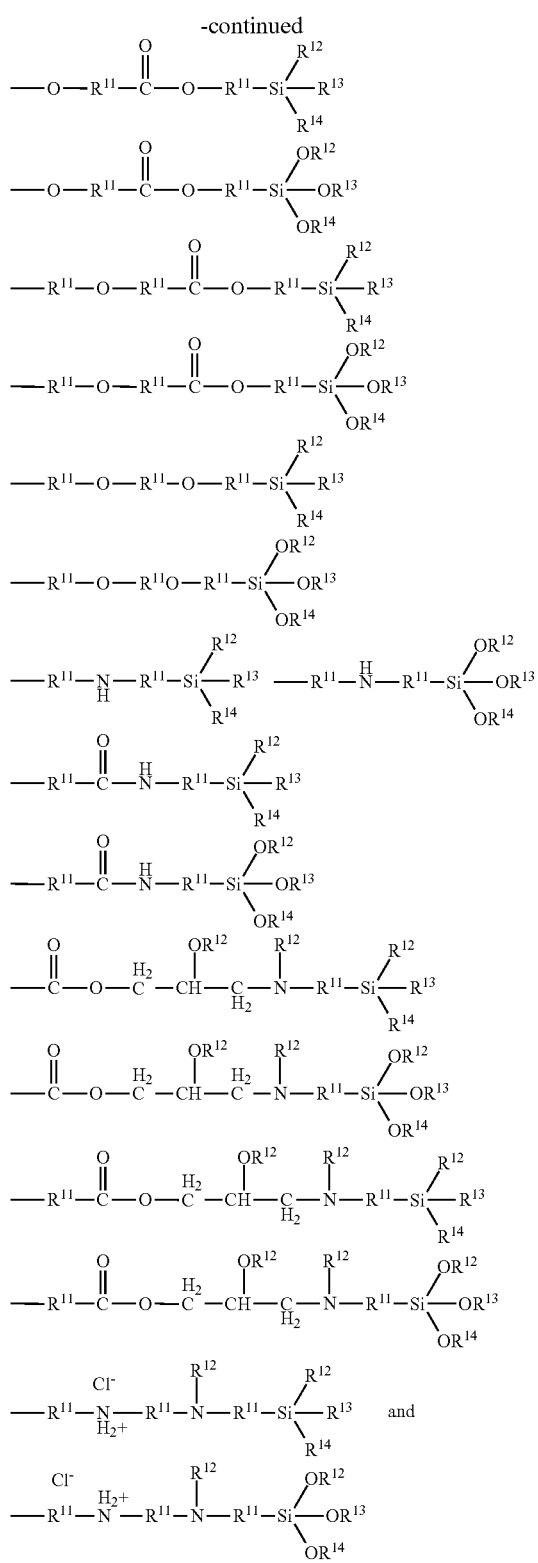

but is not limited to the illustrated examples.

In the polar functional group, $R^8$'s and $R^{11}$'s are each C1-C20 straight or branched alkylene, haloalkylene, alkenylene, or haloalkenylene; C3-C20 straight or branched alkynylene or haloalkynylene; C3-C12 cycloalkylene which is unsubstituted or substituted by alkyl, alkenyl, alkynyl, halogen, haloalkyl, haloalkenyl, or haloalkynyl; C6-C40 arylene which is unsubstituted or substituted by alkyl, alkenyl, alkynyl, halogen, haloalkyl, haloalkenyl, or haloalkynyl; or C7-C15 aralkylene which is unsubstituted or substituted by alkyl, alkenyl, alkynyl, halogen, haloalkyl, haloalkenyl, or haloalkynyl, $R^9$'s, $R^{12}$'s, $R^{13}$'s, and $R^{14}$'s are each hydrogen; halogen; C1-C20 straight or branched alkyl, haloalkyl, alkenyl, or haloalkenyl; C3-C20 straight or branched alkynyl or haloalkynyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or alkoxy, haloalkoxy, silyl, siloxy, aryloxy, haloaryloxy, carbonyloxy, or halocarbonyloxy, and k's are each an integer of 1 to 10.

In Formula 1 above, $L_3$ is an NHC ligand and may be one selected from compounds represented by Formulae 3A through 3D below, but is not limited to the illustrated examples, and all NHC compounds known in the pertinent art can also be used:

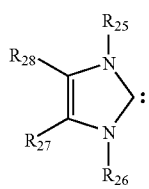
<Formula 3A>

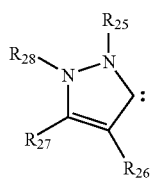
<Formula 3B>

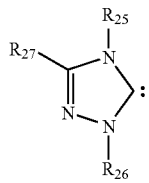
<Formula 3C>

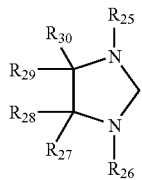
<Formula 3D> wherein $R_{25}$, $R_{26}$, $R_{27}$, $R_{28}$, $R_{29}$, and $R_{30}$ are each independently hydrogen, C1-C20 straight or branched alkyl, C3-C12 cycloalkyl, C2-C20 straight or branched alkenyl, C6-C15 cycloalkenyl, C3-C20 straight or branched allyl, C6-C30 aryl, C6-C30 heteroatom-containing aryl, or C7-C30 aralkyl, which may be optionally substituted by at least one hydrocarbyl and/or heteroatom substituent selected from C1-C5 straight or branched alkyl, C1-C5 straight or branched haloalkyl, C2-C5 straight or branched alkenyl, C2-C5 straight or branched haloalkenyl, halogen, sulfur, oxygen, nitrogen, phosphorus, and a phenyl group. Here, the phenyl group may be optionally substituted by C1-C5 straight or branched alkyl, C1-C5 straight or branched haloalkyl, halogen, or a heteroatom, but is not limited to the illustrated examples, and the alkenyl may include allyl or vinyl.

In Formula 1 above, [Ani] is an anion capable of weakly coordinating with the Group X metal M, and may be one selected from the group consisting of borate, aluminate, $[SbF_6]-$, $[PF_6]-$, $[AsF_6]-$, perfluoroacetate $[CF_3CO_2]-$, perfluoropropionate $[C_2F_5CO_2]-$, perfluorobutyrate $[CF_3CF_2CF_2CO_2]-$, perchlorate $[ClO_4]-$, p-toluenesulfonate $[p-CH_3C_6H_4SO_3]-$, $[SO_3CF_3]-$, boratabenzene, and carborane which is unsubstituted or substituted by halogen.

In more detail, in the metal catalyst complex, the borate or the aluminate may be an anion represented by Formula 4A or 4B below:

  <Formula 4A>

  <Formula 4B> wherein M' is boron or aluminum, and $R_{30}$'s are each independently halogen; C1-C20 straight or branched alkyl or alkenyl which is unsubstituted or substituted by halogen; C3-C12 cycloalkyl which is unsubstituted or substituted by halogen; C6-C40 aryl which is unsubstituted or substituted by halogen; C6-C40 aryl which is substituted by C3-C20 straight or branched trialkylsiloxy or C18-C48 straight or branched triarylsiloxy; or C7-C15 aralkyl which is unsubstituted or substituted by halogen or hydrocarbon.

According to an embodiment of the present invention, the metal catalyst complex may be represented by Formula 5 below:

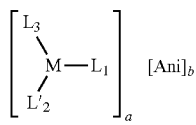  <Formula 5> wherein M, $L_1$, $L'_2$, $L_3$, [Ani], a, and b are as defined above.

More preferably, the metal catalyst complex may be selected from compounds represented by Formulae 6A through 6D below:

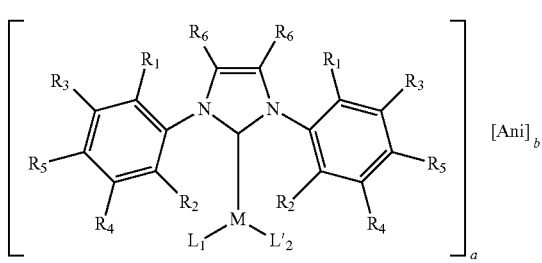  <Formula 6A>

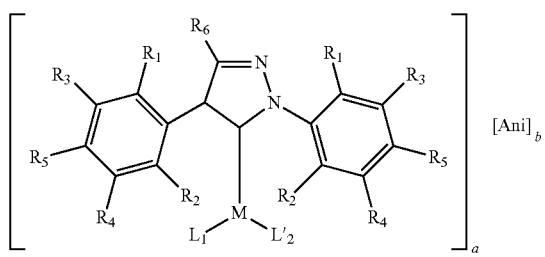  <Formula 6B>

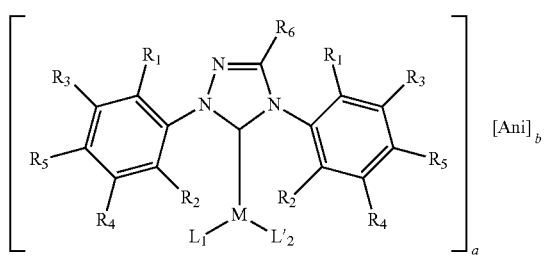  <Formula 6C>

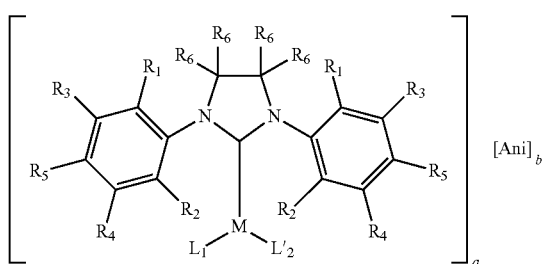  <Formula 6D> wherein M, $L_1$, $L'_2$, [Ani], a, and b are as defined above, and $R_1$ through $R_6$ are each independently hydrogen; halogen; C1-C20 straight or branched alkyl, alkoxy, or alkenyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or C3-C20 alkynyl, but are not limited to the illustrated examples, and at least one of $R_1$ through $R_6$ is halogen; or a halogen-containing alkyl, aryl, aralkyl, or alkylaryl group. The alkenyl may include allyl or vinyl. In the compounds of Formulae 6A through 6D above, $R_1$ through $R_6$ may also include a polar functional group including at least one of oxygen, nitrogen, phosphorus, sulfur, silicon, and boron, instead of halogen. The polar functional group is not particularly limited provided that it can provide an electronic effect by inducing electron withdrawal or donation. Preferably, the polar functional group may be a silyl group, a sulfonyl group, a nitro group, an amino group, a cyano group, an acetyl group, an ester group, a carbonyl group, an ether group, or the like.

Still more preferably, the metal catalyst complex may be represented by Formula 7 below:

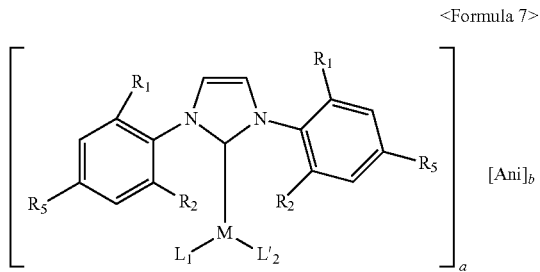

<Formula 7> wherein M, $L_1$, $L'_2$, [Ani], $R_1$, $R_2$, $R_5$, a, and b are as defined above.

Most preferably, the metal catalyst complex may be represented by Formula 8 below:

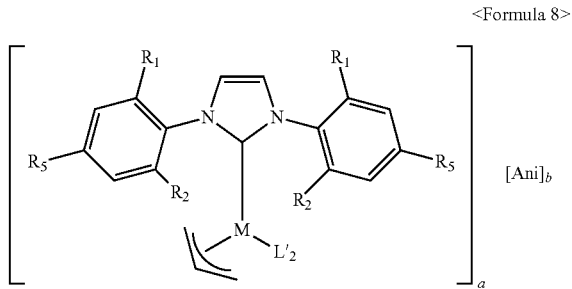

<Formula 8> wherein M, $L'_2$, [Ani], $R_1$, $R_2$, $R_5$, a, and b are as defined above, and

is C3 allyl.

More specifically, the metal catalyst complex may be represented by Formula 8A below:

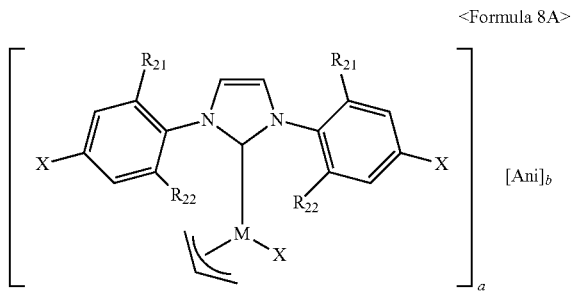

<Formula 8A> wherein a and b are as defined above, $R_{21}$ and $R_{22}$ are each independently C1-C20 straight or branched alkyl,

is C3 allyl, and

X is halogen.

The present invention also provides a precatalyst for preparing a metal catalyst complex for preparing a cyclic olefin-based polymer, which is represented by Formula 9 below:

$$M(L_1)_x(L_2)_y(L_3)_z$$ <Formula 9> wherein M, $L_1$, and $L_3$ are as defined above, $L_2$ is an anionic ligand, preferably halogen, but is not limited thereto, and may be any anionic ligand used in the pertinent art, and more specifically, may be selected from a hydrogen anion, a halogen anion, an alkoxy anion (R"O—), a carboxylate anion (R"C(O)O—), R"C(O)S—, R"C(S)O—, R"$_2$N—, or R"$_2$P— where R" is the same as $L_1$, x is 0 or 2; z is 1 or 2; and $2 \leq x+y+z \leq 6$, wherein for each of $L_1$, $L_2$, and $L_3$, when a plurality of ligands are present in a molecule of the precatalyst, the ligands may be the same or different.

In the present invention, the precatalyst may be represented by Formula 9A below:

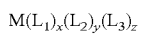

<Formula 9A> wherein M, $L_1$, and $L_3$ are as defined above, and $L_2$ is an anionic ligand. $L_2$ may be halogen or the like, but is not limited thereto. That is, $L_2$ may be any anionic ligand used in the pertinent art. More specifically, L2 may be a hydrogen anion, a halogen anion, an alkoxy anion (R"O—), a carboxylate anion (R"C(O)O—), R"C(O)S—, R"C(S)O—, R"$_2$N—, or R"$_2$P— where R" is the same as $L_1$.

The anionic ligand serves as an anionic leaving group, and thus, can be easily substituted by another ligand or a solvent.

In the present invention, the precatalyst may be selected from compounds represented by Formulae 10A through 10D below:

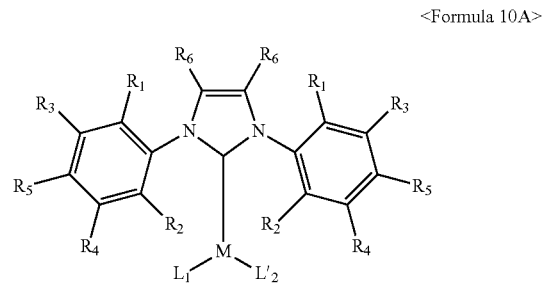

<Formula 10A>

-continued

<Formula 10B>

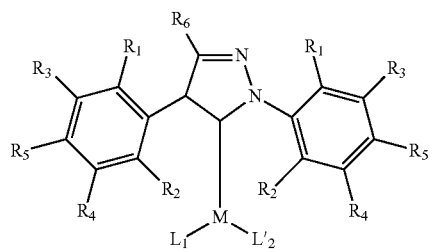

<Formula 10C>

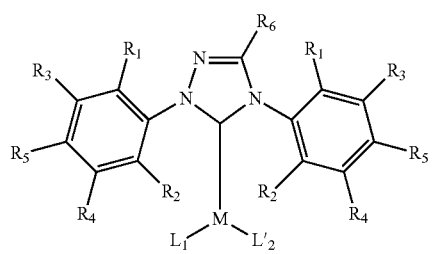

<Formula 10D>

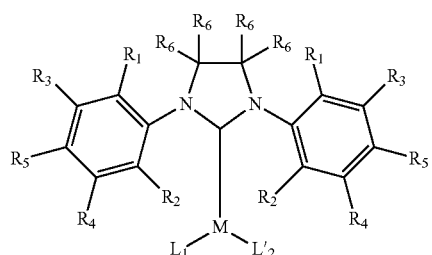

wherein M, $L_1$, $L_2$, $R_1$ through $R_6$ are as defined above, and at least one of $R_1$ through $R_6$ is halogen or a halogen-containing alkyl, aryl, aralkyl, or alkylaryl group.

More preferably, the precatalyst may be represented by Formula 11 below:

<Formula 11>

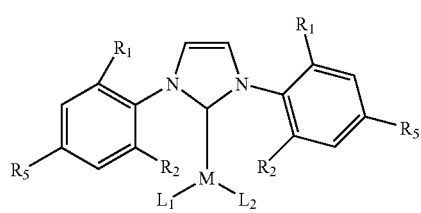

wherein M, $L_1$, $L_2$, $R_1$, $R_2$, and $R_5$ are as defined above, and at least one of $R_1$, $R_2$, and $R_5$ is halogen or a halogen-containing alkyl, aryl, aralkyl, or alkylaryl group.

Still more preferably, the precatalyst may be represented by Formula 12 below:

<Formula 12>

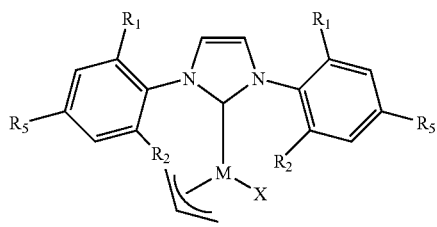

wherein M, $R_1$, $R_2$, and $R_5$ are as defined above,

is C3 allyl, and
X is halogen.

More specifically, the precatalyst may be represented by Formula 12A below:

<Formula 12A>

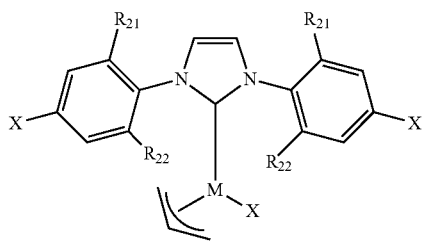

wherein $R_{21}$ and $R_{22}$ are each independently C1-C20 straight or branched alkyl,

is C3 allyl, and
X is halogen.

The precatalysts of Formulae 9 through 12A may be used in cyclic olefin polymerization, but the present invention is not limited thereto. That is, the precatalysts of Formulae 9 through 12A may also be used in all other olefin polymerization reactions wherein a metal complex is used as a catalyst or a precatalyst.

Most preferably, the precatalyst may be [chloro($\eta^3$-allyl)-(N,N-bis(4-bromo-2,6-dimethylphenyl)imidazol-2-ylidene)-palladium], [chloro($\eta^3$-allyl)-(N,N-bis(4-iodo-2,6-diisopropylphenyl)imidazol-2-ylidene)-palladium], [chloro($\eta^3$-allyl)-(N,N-bis(4-bromo-2,6-diisopropylphenyl)imidazol-2-ylidene)-palladium], or the like.

The present invention also provides a method of preparing the precatalyst.

First, an amine compound represented by Formula 13 below reacts with glyoxal to prepare a diimine compound represented by Formula 14 below. Then, the dimine compound of Formula 14 reacts with aldehyde in an acidic condition to prepare an imidazolium salt represented by Formula 15 below. Then, the imidazolium salt of Formula 15 reacts with an alkoxide compound to prepare a free carbene represented by Formula 16 below. Finally, the free carbene of Formula 16 reacts with a Group X metal compound to prepare a precatalyst as represented by Formula 12 above:

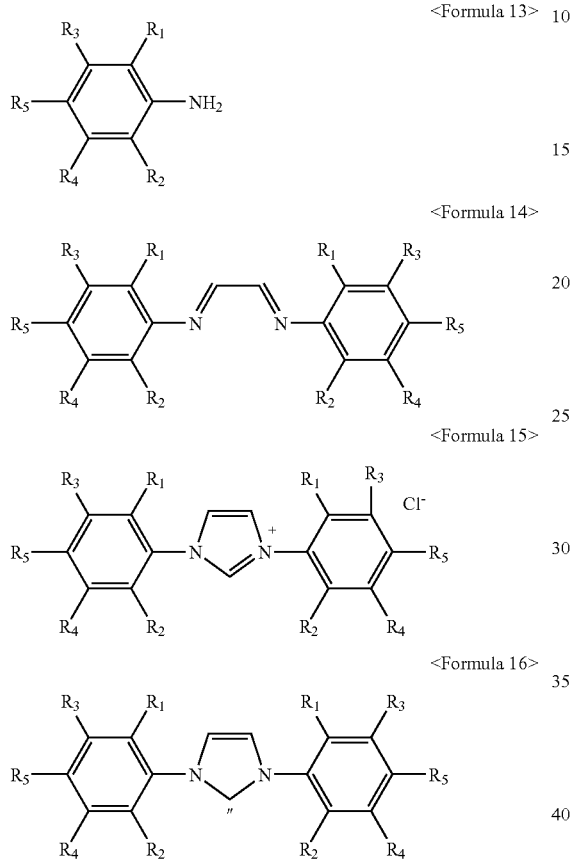

wherein $R_1$ through $R_5$ are as defined above. A method of preparing a precatalyst according to an embodiment of the present invention is represented by Reaction Scheme 1 below:

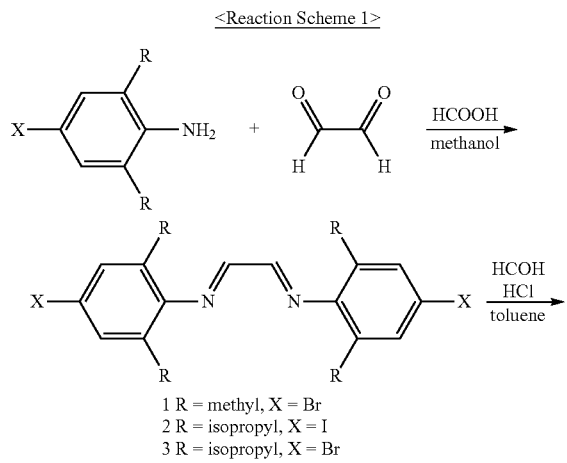

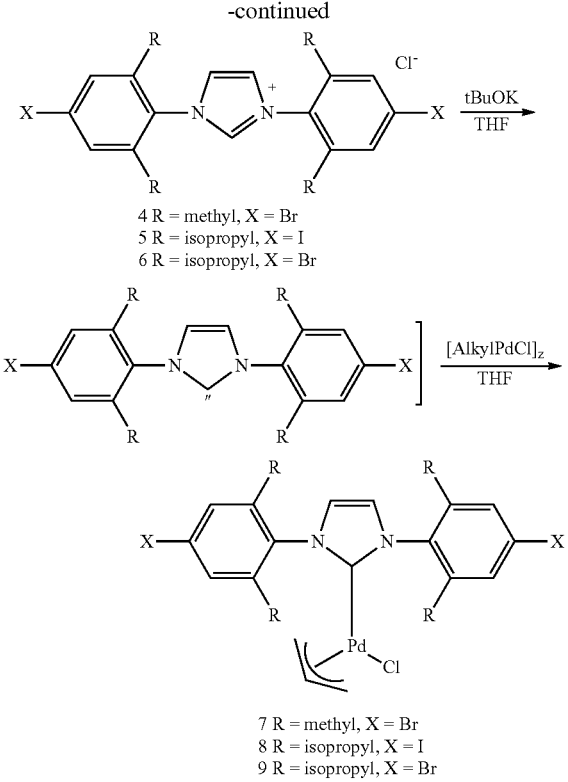

The present invention also provides a method of preparing a metal catalyst complex for preparing a cyclic olefin-based polymer by addition polymerization of a cyclic olefin-based monomer, the method including contacting a precatalyst according to an embodiment of the present invention with a salt compound represented by Formula 17 below:

$$[Cat]_a[Ani]_b \qquad \text{<Formula 17>}$$

wherein a and b are each 1 to 10; [Cat] is a cation selected from the group consisting of a hydrogen ion (H⁺), an alkaline metal cation, a transition metal cation, and a cation-containing functional group; and [Ani] is an anion capable of weakly coordinating with the metal M of the precatalyst and is as defined above.

A method of preparing a metal catalyst complex according to an embodiment of the present invention is represented by Reaction Scheme 2 below.

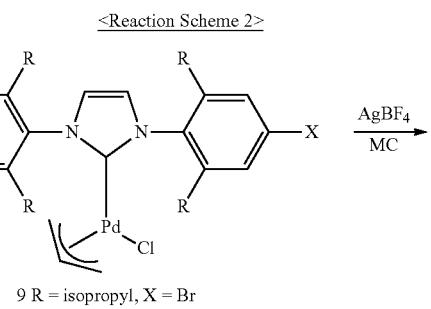

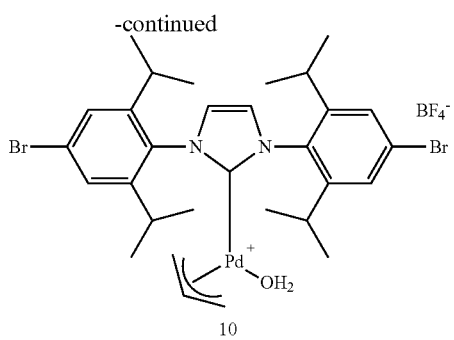

In the method of preparing the metal catalyst complex, the precatalyst and the salt compound may be dissolved in an organic solvent selected from the group consisting of dichloromethane, dichloroethane, toluene, chlorobenzene, and a mixture thereof.

In the method of preparing the metal catalyst complex, the ratio of the salt compound to the precatalyst may be 0.5 to 10 moles based on 1 mole of the precatalyst. If the ratio of the salt compound to the precatalyst is less than 0.5 moles, the yield of a metal catalyst complex may be lowered. On the other hand, if it exceeds 10 moles, unwanted side reactions may occur.

Hereinafter, the present invention will be described more specifically with reference to the following working examples. The following working examples are for illustrative purposes only and are not intended to limit the scope of the invention.

In the following working examples, all manipulations for treating compounds susceptible to air or water were carried out using standard Schlenk technique or glove box technique. NMR spectra were obtained using a Bruker 300 spectrometer. $^1$H NMR spectrum and $^{13}$C NMR spectrum were measured at 300 MHz and 75 MHz, respectively. The molecular weights and molecular weight distributions of polymers were measured by GPC (gel permeation chromatography) using standard polystyrene samples. Thermogravimetric analysis (TGA) was made using TA Instrument (TGA 2050; heating rate: 10 K/min). Toluene was purified by distillation from potassium/benzophenone, and dichloromethane and chlorobenzene were purified by distillation from $CaH_2$.

Synthesis of Monomers

Synthesis Example 1

Synthesis of 5-norbornene-2-carboxylic Acid Methylester (Monomer b) (Endo:Exo=100:0)

5-norbornene-2-carboxylic acid (a mixture of endo- and exo-isomers) (3.8 g, 27.5 mmol) was dissolved in distilled water. A solution of $I_2$ (9.4 g, 37.1 mmol) and KI (19 g, 114 mmol) in 112 ml of distilled water was added to the reaction mixture, and the resultant mixture was incubated at room temperature for three hours. After the reaction was terminated, the resultant solution was extracted with ethylether. A solvent was removed from the organic layer to obtain oily iodolactone. This compound was dissolved in a trace amount of ethylacetate, and the resultant solution was recrystallized with hexane to give pure crystalline iodolactone (yield: 50%).

The iodolactone (4.4 g, 16.6 mmol) was dissolved in 70 ml of glacial acetic acid. The resultant solution was cooled to 0° C. and zinc dust (21.5 g, 328 mmol) was gradually added thereto. The reaction mixture was incubated at 15° C. for three hours and then at room temperature for two hours. An undissolved inorganic matter was filtered out, and the filtrate was diluted with water and extracted with ethylether. The organic layer was collected, dried over anhydrous $MgSO_4$, and purified by fractional distillation to obtain 5-norbornene-2-carboxylic acid (endo-isomer). The endo-isomer and $Na_2CO_3$ were dissolved in acetone, and $CH_3I$ was gradually added thereto. A solvent was removed from the resultant solution followed by silica column chromatography to give a pure endo-isomer (monomer b).

Synthesis Example 2

Synthesis of 5-norbornene-2-carboxylic Acid Methylester (Monomer b) (Endo:Exo=5:95)

5-norbornene-2-carboxylic acid (a mixture of endo- and exo-isomers) (3.8 g, 27.5 mmol) was dissolved in distilled water. A solution of $I_2$ (9.4 g, 37.1 mmol) and KI (19 g, 114 mmol) in 112 ml of distilled water was added to the reaction mixture, and the resultant mixture was incubated at room temperature for three hours. After the reaction was terminated, the resultant solution was extracted with ethylether. The aqueous layer was oxidized with 5% $H_2SO_4$, and extracted with ethylether. A solvent was remove from the organic layer, and the residue was purified by fractional distillation to obtain 5-norbornene-2-carboxylic acid (a mixture of endo- and exo-isomers, endo:exo=5:95). This compound and $Na_2CO_3$ were dissolved in acetone, and $CH_3I$ was gradually added thereto. A solvent was removed from the resultant solution followed by silica column chromatography to give an exo-isomer (monomer b).

Preparation of Precatalysts

Example 1

Preparation of Compound 1 (ArN=CH—CH=NAr, Ar=2,6-Me$_2$-4-BrC$_6$H$_2$)

4-bromo-2,6-dimethyl aniline (5.6 g, 28 mmol) and glyoxal (40% solution, 1.58 ml (14 mmol)) were dissolved in methanol (30 ml), and formic acid (1 ml) was added thereto. The reaction mixture was stirred for 48 hours. The resultant solution was filtered and dried in vacuum to give a compound 1 as a yellow crystal (4.1 g, yield: 70%).

$^1$H NMR (CDCl$_3$): 8.06 (s, 2H), 7.24 (s, 4H), 2.15 (s, 12H),
$^{13}$C NMR (CDCl$_3$): 163.98, 149.08, 131.37, 129.07, 118.16, 18.52
HRMS m/z calcd: 419.9386, obsd: 419.9387

Example 2

Preparation of Compound 2 (ArN=CH—CH=NAr, Ar=2,6-iPr$_2$-4-IC$_6$H$_2$)

4-iodo-2,6-diisopropyl aniline (8.5 g, 28 mmol) and glyoxal (40% solution, 1.58 ml (14 mmol)) were dissolved in methanol (30 ml), and formic acid (1 ml) was added thereto. The reaction mixture was stirred for 48 hours. The resultant solution was filtered and dried in vacuum to give a compound 2 as a yellow crystal (6.4 g, yield: 73%).

$^1$H NMR (CDCl$_3$): 8.04 (s, 2H), 7.28 (s, 4H), 2.85 (m, 4H), 1.16 (d, 12H, 6.9 Hz),
$^{13}$C NMR (CDCl$_3$): 163.53, 149.06, 139.66, 132.91, 90.57, 28.44, 23.58
HRMS m/z calcd: 628.0811, obsd: 628.0812

Example 3

Preparation of Compound 3 (ArN=CH—CH=NAr, Ar=2,6-iPr$_2$-4-BrC$_6$H$_2$)

4-bromo-2,6-diisopropyl aniline (7.2 g, 28 mmol) and glyoxal (40% solution, 1.58 ml (14 mmol)) were dissolved in methanol (30 ml), and formic acid (1 ml) was added thereto. The reaction mixture was stirred for 48 hours. The resultant solution was filtered and dried in vacuum to give a compound 3 as a yellow crystal (5.2 g, yield: 70%).

$^1$H NMR (CDCl$_3$): 8.07 (s, 2H), 7.32 (s, 4H), 2.87 (m, 4H), 1.18 (d, 12H, 6.9 Hz), $^{13}$C NMR (CDCl$_3$): 163.68, 147.26, 139.50, 126.90, 119.24, 90.57, 28.59, 23.63

HRMS m/z calcd: 532.1088, obsd: 532.1089

Example 4

Preparation of Compound 4 [N,N-bis(4-bromo-2,6-dimethylphenyl)imidazolium chloride]

The compound 1 (3 g, 7.1 mmol) and para-formaldehyde (0.22 g, 7.1 mmol) were dissolved in toluene (30 ml) and refluxed at 100° C. until para-formaldehyde was completely dissolved. The resultant solution was cooled to 40° C., and 4M HCl in dioxane (1.7 ml, 7.1 mmol) was gradually added thereto. Then, the reaction mixture was cooled to 70° C., refluxed for about one hour, stirred at room temperature for three hours, filtered, and dried in vacuum to give a compound 4 as a gray powder (1.8 g, yield: 54%).

$^1$H NMR (CDCl$_3$): 11.65 (s, 1H), 7.56 (s, 2H), 7.40 (s, 4H), 2.22 (s, 12H)

$^{13}$C NMR (CDCl$_3$): 137.70, 137.34, 132.57, 131.96, 125.23, 124.71

HRMS m/z calcd: 432.9914, obsd: 432.9911

Example 5

Preparation of Compound 5 [N,N-bis(4-iodo-2,6-diisopropylphenyl)imidazolium chloride]

The compound 2 (4.5 g, 7.1 mmol) and para-formaldehyde (0.22 g, 7.1 mmol) were dissolved in toluene (30 ml) and refluxed at 100° C. until para-formaldehyde was completely dissolved. The resultant solution was cooled to 40° C., and 4M HCl in dioxane (1.7 ml, 7.1 mmol) was gradually added thereto. Then, the reaction mixture was cooled to 70° C., refluxed for about one hour, stirred at room temperature for three hours, filtered, and dried in vacuum to give a compound 5 as a gray powder (2.7 g, yield: 60%).

$^1$H NMR (C2D6SO): 10.24 (s, 1H), 8.55 (s, 2H), 7.81 (s, 4H), 4.25 (m, 4H), 1.24 (d, 12H, 6.9 Hz), 1.14 (d, 12H, 6.9 Hz)

HRMS m/z calcd: 628.0811, obsd: 628.0812

Example 6

Preparation of Compound 6 [N,N-bis(4-bromo-2,6-diisopropylphenyl)imidazolium chloride]

The compound 3 (3.8 g, 7.1 mmol) and para-formaldehyde (0.22 g, 7.1 mmol) were dissolved in toluene (30 ml) and refluxed at 100° C. until para-formaldehyde was completely dissolved. The resultant solution was cooled to 40° C., and 4M HCl in dioxane (1.7 ml, 7.1 mmol) was gradually added thereto. Then, the reaction mixture was cooled to 70° C., refluxed for about one hour, stirred at room temperature for three hours, filtered, and dried in vacuum to give a compound 6 as a gray powder (2.32 g, yield: 60%).

$^1$H NMR (CDCl$_3$): 11.24 (s, 1H), 7.76 (s, 2H), 7.45 (s, 4H), 2.36 (m, 4H), 1.24 (dd, 12H, 5.7 Hz)

HRMS m/z calcd: 545.1166, obsd: 545.1167

Example 7

Preparation of Compound 7 [chloro($\eta^3$-allyl)-(N,N-bis(4-bromo-2,6-dimethylphenyl)imidazol-2-ylidene)-palladium]

The compound 4 (1.5 g, 3.2 mmol) and potassium tert-butoxide (0.39 g, 3.2 mmol) were dissolved in tetrahydrofuran. The reaction mixture was stirred for four hours and a solvent was removed in vacuum. The residue was dissolved in toluene in a glove box and the resultant solution was filtered through a column packed with cellite. Toluene was removed in a reduced pressure to obtain a carbene compound as a gray solid (0.9 g, 65%). The carbene compound (0.9 g, 2.1 mmol) and allyl palladium chloride dimer [(ally)PdCl]$_2$ (0.38 g, 1.05 mmol) were dissolved in tetrahydrofuran, and the reaction mixture was stirred for one hour. Then, a solvent was removed in a reduced pressure, and the residue was washed with pentane to give a compound 7 as a gray powder (1.2 g, 92%).

$^1$H NMR (300 Mz, CDCl$_3$): 7.33 (s, 4H), 7.11 (s, 2H), 4.91 (m, 1H), 3.95 (d, 1H), 3.21 (d, 1H), 2.87 (d, 1H), 2.23 (s, 6H), 2.21 (s, 6H), 1.82 (d, 1H).

$^1$H NMR (CDCl$_3$): 7.33 (s, 4H), 7.11 (s, 2H), 4.91 (sep, 1H, 9 Hz), 3.95 (dd, 1H, 1.5 Hz), 3.21 (d, 1H, 6 Hz), 2.87 (d, 1H, 13.5 Hz), 2.22 (d, 12H, 10.2 Hz), 1.82 (d, 1H, 11.7 Hz)

$^{13}$C NMR (CDCl$_3$): 138.32, 137.60, 132.42, 131.70, 123.45, 123.37, 115.07, 77.62, 73.52, 49.97, 18.67

HRMS m/z calcd: 578.9262, obsd: 578.9263

Example 8

Preparation of Compound 8 [chloro($\eta^3$-allyl)-(N,N-bis(4-iodo-2,6-diisopropylphenyl)imidazol-2-ylidene)-palladium]

The compound 5 (2.0 g, 3.2 mmol) and potassium tert-butoxide (0.39 g, 3.2 mmol) were dissolved in tetrahydrofuran. The reaction mixture was stirred for four hours and a solvent was removed in vacuum. The residue was dissolved in toluene in a glove box and the resultant solution was filtered through a column packed with cellite. Toluene was removed in a reduced pressure to obtain a carbene compound as a gray solid (1.24 g, 65%). The carbene compound (1.24 g, 2.1 mmol) and allyl palladium chloride dimer [(ally)PdCl]$_2$ (0.38 g, 1.05 mmol) were dissolved in tetrahydrofuran, and the reaction mixture was stirred for one hour. Then, a solvent was removed in a reduced pressure, the residue was washed with pentane, and the resultant solid product was filtered to give a compound 8 as a gray powder (1.49 g, 90%).

$^1$H NMR (CDCl$_3$): 7.50 (s, 4H), 7.01 (s, 2H), 4.78 (m, 1H, 7.2 Hz), 3.89 (dd, 1H, 1.5 Hz), 2.97 (dd, 1H, 6 Hz), 2.95 (dd, 2H, 6.9 Hz), 2.68 (dd, 2H, 6.6 Hz), 1.57 (d, 1H, 12.3 Hz), 1.28 (d, 6H, 6.6 Hz), 1.22 (d, 6H, 6.6 Hz), 1.08 (d, 6H, 6.6 Hz), 0.98 (d, 6H, 6.6 Hz)

$^{13}$C NMR (CDCl$_3$): 145.53, 132.54, 130.30, 127.61, 127.43, 126.29, 125.13, 68.29, 29.48, 25.96, 24.99, 24.27, 13.54, 12.74

HRMS m/z calcd: 787.0237, obsd: 787.0238

Example 9

Preparation of Compound 9 [chloro($\eta^3$-allyl)-(N,N-bis(4-bromo-2,6-diisopropylphenyl)imidazol-2-ylidene)-palladium]

The compound 6 (1.74 g, 3.2 mmol) and potassium tert-butoxide (0.39 g, 3.2 mmol) were dissolved in tetrahydrofuran. The reaction mixture was stirred for four hours and a solvent was removed in vacuum. The residue was dissolved in toluene in a glove box and the resultant solution was filtered through a column packed with cellite. Toluene was removed in a reduced pressure to obtain a carbene compound as a gray solid (1.02 g, 63%). The carbene compound (1.02 g, 2.0 mmol) and allyl palladium chloride dimer [(allyl)PdCl]$_2$ (0.36 g, 1.0 mmol) were dissolved in tetrahydrofuran, and the reaction mixture was stirred for one hour. Then, a solvent was removed in a reduced pressure, the residue was washed with pentane, and the resultant solid product was filtered to give a compound 9 as a gray powder (1.24 g, 90%).

$^1$H NMR (CDCl$_3$): 7.37 (s, 4H), 7.13 (s, 2H), 4.84 (m, 1H, 5.7 Hz), 3.95 (dd, 1H, 1.5 Hz), 3.08 (m, 3H), 2.84 (d, 1H, 13.5 Hz), 2.78 (dd, 2H, 6.9 Hz), 1.62 (s, 1H), 1.36 (d, 6H, 6.6 Hz), 1.30 (d, 6H, 6.6 Hz), 1.16 (d, 6H, 6.6 Hz), 1.06 (d, 6H, 6.6 Hz)

$^{13}$C NMR (CDCl$_3$): 145.5, 132.5, 130.3, 127.6, 127.4, 126.2, 125.1, 68.2, 29.4, 25.9, 24.9, 24.2, 13.5, 12.7

HRMS m/z calcd: 691.0514, obsd: 691.0516

The compounds 1-9 prepared in Examples 1-9 are as represented by Reaction Scheme 1 above.

Preparation of Metal Catalyst Complexes

Catalysts

Example 10

Preparation of Compound 10

The compound 9 (0.2 g, 0.351 mmol) and AgBF$_4$ (68 mg, 0.351 mmol) were dissolved in 5 ml of CH$_2$Cl$_2$ and the reaction mixture was stirred for one hour. The reaction solution was filtered through cellite and a solvent was removed to give a compound 10 as a gray powder (0.2 g, 92%).

$^1$H NMR (CDCl$_3$): 7.43 (s, 4H), 7.24 (s, 2H), 4.84 (m, 1H), 4.45 (br, 1H), 3.34 (br, 1H), 2.64 (br, 4H), 2.32 (m, 1H), 2.21 (m, 1H), 1.30 (m, 12H), 1.19 (m, 12H)

The X-ray crystallographic structure of the compound 10 is illustrated in FIG. 1.

Preparation of Homopolymers and Copolymers

Monomers and precatalysts used in polymerization reactions below are as follows.

Monomers

a

b

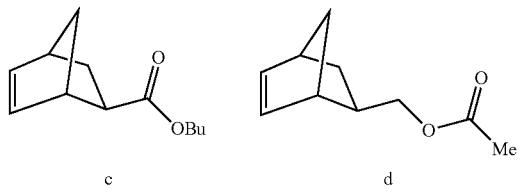
c          d

Precatalysts

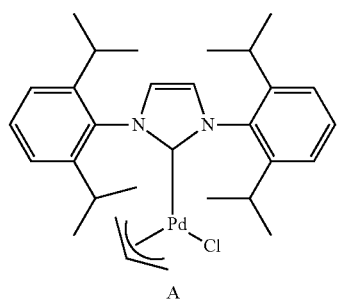
A

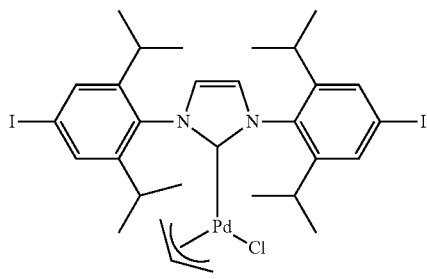
B

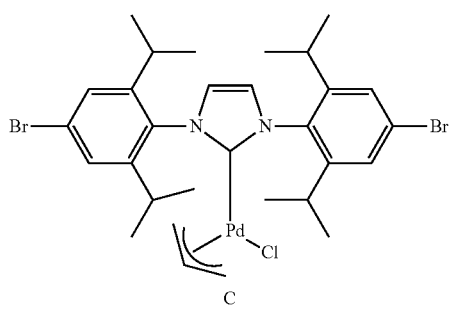
C

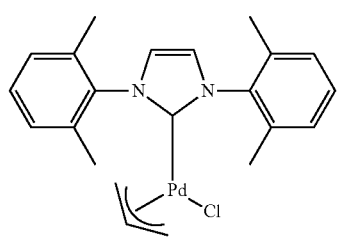
D

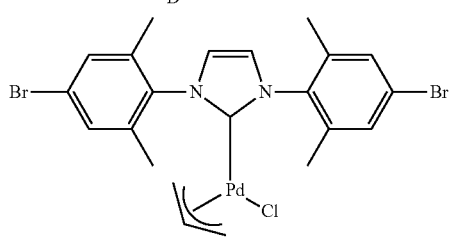
E

Example 11

Homopolymerization of Norbornene (Monomer a)

Norbornene (5 g, 53.1 mmol) was added to a 100 ml Schlenk flask containing toluene (15 mL). The precatalyst B and silver tetrafluoroborate (AgBF$_4$) were dissolved in 5 ml of a mixed solution of methylene chloride and toluene (1:1) in a glove box, and the reaction mixture was stirred for one hour. Then, the palladium catalyst (0.53 mmol) filtered through a column packed with cellite was added to the flask, and the flask was stirred at 25□ for 20 hours. Then, the resultant solution was added to excess methanol to obtain a white polymer precipitate. The precipitate was filtered through a glass funnel, and the recovered product was dried in a vacuum oven at 80□ for 24 hours to give a norbornene polymer (yield: 99%).

Example 12

A norbornene polymer was prepared in the same manner as in Example 11 using the same catalyst amount, polymerization solvent, and polymerization time as in Example 11 and the precatalyst C as summarized in Table 1 below.

Example 13

A norbornene polymer was prepared in the same manner as in Example 11 using the same catalyst amount, polymerization solvent, and polymerization time as in Example 11 and the precatalyst E as summarized in Table 1 below.

Comparative Example 1

A norbornene polymer was prepared in the same manner as in Example 11 using the same catalyst amount, polymerization solvent, and polymerization time as in Example 11 and the precatalyst A as summarized in Table 1 below.

Comparative Example 2

A norbornene polymer was prepared in the same manner as in Example 11 using the same catalyst amount, polymerization solvent, and polymerization time as in Example 11 and the precatalyst D as summarized in Table 1 below.

TABLE 1

| | Monomer | Precatalyst | [M]/precatalyst | [Ani] | Time (h) | Solvent | Mn | Mw | Mw/Mn[2] | Yield (%)[3] |
|---|---|---|---|---|---|---|---|---|---|---|
| Example 11 | a | B | 100/1 | BF$_4^-$ | 20 | Toluene | | | Not measured[1] | 99 |
| Example 12 | a | C | 100/1 | BF$_4^-$ | 20 | Toluene | | | Not measured[1] | 99 |
| Example 13 | a | E | 100/1 | BF$_4^-$ | 20 | Toluene | | | Not measured[1] | 99 |
| Comparative Example 1 | a | A | 100/1 | BF$_4^-$ | 20 | Toluene | | | Not measured[1] | 99 |
| Comparative Example 2 | a | D | 100/1 | BF$_4^-$ | 20 | Toluene | | | Not measured[1] | 30 |

[1] not dissolved in tetrahydrofuran
[2] measured by GPC using standard polystyrene
[3] yield after completely separated

Example 14

Polymerization of 5-norbornene-2-allylacetate (Exo:Endo=40:60, Monomer d)

5-norbornene-2-allylacetate (exo:endo=40:60, 5 ml (30.9 mmol)) was added to a 100 ml Schlenk flask containing 15 ml of toluene. The precatalyst B and silver tetrafluoroborate (AgBF$_4$) were dissolved in 5 ml of a mixed solution of methylene chloride and toluene (1:1) in a glove box, and the reaction mixture was stirred for one hour. Then, the palladium catalyst (0.031 mmol) filtered through a column packed with cellite was added to the flask, and the flask was stirred at 25° C. for 20 hours. Then, the resultant solution was added to excess methanol to obtain a white polymer precipitate. The precipitate was filtered through a glass funnel, and the recovered product was dried in a vacuum oven at 80° C. for 24 hours to give a norbornene polymer (yield: 62%).

Example 15

A norbornene polymer was prepared in the same manner as in Example 14 using the same catalyst amount, polymerization solvent, and polymerization time as in Example 14 and the precatalyst C as summarized in Table 2 below.

Comparative Example 3

A norbornene polymer was prepared in the same manner as in Example 14 using the same catalyst amount, polymerization solvent, and polymerization time as in Example 14 and the precatalyst A as summarized in Table 2 below.

TABLE 2

| | Monomer | Precatalyst | [M]/ precatalyst | [Ani] | Time (h) | Solvent | Mn | Mw | Mw/ Mn[2] | Yield (%)[3] |
|---|---|---|---|---|---|---|---|---|---|---|
| Example 14 | d(40:60)[1] | B | 1000/1 | $BF_4^-$ | 20 | Toluene | 52,370 | 103,692 | 1.98 | 62 |
| Example 15 | d(40:60)[1] | C | 1000/1 | $BF_4^-$ | 20 | Toluene | 47,940 | 89,648 | 1.87 | 57 |
| Comparative Example 3 | d(40:60)[1] | A | 1000/1 | $BF_4^-$ | 20 | Toluene | 40,554 | 77,864 | 1.92 | 55 |

[1] numbers in parentheses represent a ratio of endo- and exo-isomers
[2] measured by GPC using standard polystyrene
[3] yield after completely separated

Example 16

Copolymerization of Norbornene (Monomer a) and 5-norbornene-2-carboxylic Acid Methylester (Monomer b) (3:1)

Norbornene (3 g, 31.9 mmol), 5-norbornene-2-carboxylic acid methylester (1.6 ml, 10.6 mmol), and toluene (14 ml) were added to a 100 ml Schlenk flask. The precatalyst B and silver tetrafluoroborate ($AgBF_4$) were dissolved in 5 ml of a mixed solution of methylene chloride and toluene (1:1) in a glove box, and the reaction mixture was stirred for one hour. Then, the palladium catalyst (0.42 mmol) filtered through a column packed with cellite was added to the flask, and the flask was stirred at 25° C. for 20 hours. Then, the resultant solution was added to excess methanol to obtain a white copolymer precipitate. The precipitate was filtered through a glass funnel, and the recovered product was dried in a vacuum oven at 80° C. for 24 hours to give a polymer (yield: 70%).

Example 17

A polymer was prepared in the same manner as in Example 16 using the same catalyst amount, polymerization solvent, and polymerization time as in Example 16 and the precatalyst C as summarized in Table 3 below.

Comparative Example 4

A polymer was prepared in the same manner as in Example 16 using the same catalyst amount, polymerization solvent, and polymerization time as in Example 16 and the precatalyst A as summarized in Table 3 below.

Example 18

Copolymerization of Norbornene (Monomer a) and 5-norbornene-2-carboxylic Acid Methylester (Monomer b) (3:1)

Norbornene (3 g, 31.9 mmol), 5-norbornene-2-carboxylic acid methylester (1.6 ml, 10.6 mmol), and toluene (14 ml) were added to a 100 ml Schlenk flask. The precatalyst C and silver hexafluoroantimonate ($AgSbF_6$) were dissolved in chlorobenzene in a glove box, and the reaction mixture was dissolved for one hour. Then, the palladium catalyst (0.42 mmol) filtered through a column packed with cellite was added to the flask, and the flask was stirred at 25° C. for 12 hours. Then, the resultant solution was added to excess methanol to obtain a white copolymer precipitate. The precipitate was filtered through a glass funnel, and the recovered product was dried in a vacuum oven at 80° C. for 24 hours to give a polymer (yield: 98%).

TABLE 3

| | Monomer | Precatalyst | [Ani] | Time (h) | Solvent | Mn | Mw | Mw/Mn[3] | Monomer ratio[4] | Yield (%)[5] |
|---|---|---|---|---|---|---|---|---|---|---|
| Example 16 | a + b (3:1)[1] | B | $BF_4^-$ | 20 | Toluene/$CH_2Cl_2$ | | | Not measured[2] | | 70 |
| Example 17 | a + b (3:1)[1] | C | $BF_4^-$ | 20 | Toluene/$CH_2Cl_2$ | | | Not measured[2] | | 75 |
| Comparative Example 4 | a + b (3:1)[1] | A | $BF_4^-$ | 20 | Toluene/$CH_2Cl_2$ | | | Not measured[2] | | 71 |
| Example 18 | a + b (3:1)[1] | C | $BF_4^-$ | 12 | Chlorobenzene | | | Not measured[2] | | 98 |

[1] numbers in parentheses represent a molar ratio of monomer a and monomer b (a ratio of endo:exo in monomer b is 5:95)
[2] not dissolved in tetrahydrofuran
[3] measured by GPC using standard polystyrene
[4] measured using NMR
[5] yield after completely separated

Example 19

Copolymerization of Norbornene (Monomer a) and 5-norbornene-2-carboxylic Acid Butylester (Monomer c) (3:1)

Norbornene (3 g, 31.9 mmol), 5-norbornene-2-carboxylic acid butylester (1.54 ml, 10.6 mmol), and toluene (14 ml) were applied to a 100 ml Schlenk flask. The precatalyst B and silver tetrafluoroborate ($AgBF_4$) were dissolved in 5 ml of a mixed solution of methylene chloride and toluene (1:1) in a glove box, and the reaction mixture was stirred for one hour. Then, the palladium catalyst (0.42 mmol) filtered through a column packed with cellite was added to the flask, and the flask was stirred at 25° C. for 20 hours. Then, the resultant solution was added to excess methanol to obtain a white copolymer precipitate. The precipitate was filtered through a glass funnel, and the recovered product was dried in a vacuum oven at 80° C. for 24 hours to give a polymer (yield: 72%).

Example 20

A polymer was prepared in the same manner as in Example 19 using the same catalyst amount, polymerization solvent, and polymerization time as in Example 19 and the precatalyst C as summarized in Table 4 below.

Comparative Example 5

A polymer was prepared in the same manner as in Example 19 using the same catalyst amount, polymerization solvent, and polymerization time as in Example 19 and the precatalyst A as summarized in Table 4 below.

Example 21

Copolymerization of Norbornene (Monomer a) and 5-norbornene-2-carboxylic Acid Butylester (Monomer c) (3:1)

Norbornene (3 g, 31.9 mmol), 5-norbornene-2-carboxylic acid butylester (1.54 ml, 10.6 mmol), and toluene (14 ml) were applied to a 100 ml Schlenk flask. The precatalyst C and silver hexafluoroantimonate ($AgSbF_6$) were dissolved in 5 ml of chlorobenzene in a glove box, and the reaction mixture was stirred for one hour. Then, a palladium catalyst (0.42 mmol) filtered through a column packed with cellite was added to the flask, and the flask was stirred at 25° C. for 12 hours. Then, the resultant solution was added to excess methanol to obtain a white copolymer precipitate. The precipitate was filtered through a glass funnel, and the recovered product was dried in a vacuum oven at 80° C. for 24 hours to give a polymer (yield: 87%).

TABLE 4

| | Monomer | Precatalyst | [Ani] | Time (h) | Solvent | Mn | Mw | Mw/Mn[3] | Monomer ratio[4] | Yield (%)[5] |
|---|---|---|---|---|---|---|---|---|---|---|
| Example 19 | a + c (3:1)[1] | B | $BF_4^-$ | 20 | Toluene/$CH_2Cl_2$ | 25,023 | 41,180 | 1.64 | 84:16 (a:c) | 70 |
| Example 20 | a + c (3:1)[1] | C | $BF_4^-$ | 20 | Toluene/$CH_2Cl_2$ | 11,763 | 24,198 | 2.05 | 83:17 (a:c) | 76 |
| Comparative Example 5 | a + c (3:1)[1] | A | $BF_4^-$ | 20 | Toluene/$CH_2Cl_2$ | 17,642 | 40,451 | 2.29 | 81:19 (a:c) | 72 |
| Example 21 | a + c (3:1)[1] | C | $SbF_6^-$ | 12 | Chlorobenzene | Not measured[2] | | | 79:21 (a:c) | 87 |

[1] numbers in parentheses represent a molar ratio of monomer a and monomer c (a ratio of endo:exo in monomer c is 5:95)
[2] not dissolved in tetrahydrofuran
[3] measured by GPC using standard polystyrene
[4] measured using NMR
[5] yield after completely separated As can be seen in the above working examples, in a metal catalyst complex for cyclic olefin polymerization according to the present invention, a carbene ligand having a functional group capable of providing an electronic effect of a ligand is coordinated to metal. Thus, the use of the metal catalyst complex of the present invention can increase the weight average molecular weight ($M_w$) or yield of a polymer, compared with the use of a catalyst having no electronic effect of a ligand.

In particular, considering that norbornene including a polar substituent generally has low reactivity, the preparation of a norbornene polymer having a higher yield and Mw of 5,000 or more in the presence of the metal catalyst complex of the present invention is considered to have commercial importance.

The metal catalyst complex of the present invention has an N-heterocyclic carbene ligand, and thus, is excellent in thermal stability and reactivity.

What is claimed is:

1. A metal catalyst complex for preparing a cyclic olefin-based polymer by addition polymerization of a cyclic olefin-based monomer, which is represented by Formula 1 below:

$$[M(L_1)_x(L'_2)_y(L_3)_z]_a[Ani]_b \qquad <\text{Formula 1}>$$

wherein M is a Group X metal,
$[M(L_1)_x(L'_2)_y(L_3)_z]$ is a cationic complex,
$L_1$ is an anionic hydrocarbyl-containing ligand,
$L'_2$ is a neutral ligand,
$L_3$ is an N-heterocyclic carbene ligand,
[Ani] is $BF_4^-$,
x is 1 or 2; y is 0 to 4; z is 1 or 2; $2 \leq x+y+z \leq 6$,
a and b are respectively the number of cations and the number of anions capable of weakly coordinating with the metal M and are each a number of 1-10 which is used to satisfy the net charge balance of the metal catalyst complex,
wherein for each of $L_1$, $L'_2$, and $L_3$, when a plurality of ligands are present in a molecule of the metal catalyst complex, the ligands may be the same or different.

2. The metal catalyst complex of claim 1, wherein the cyclic olefin-based monomer is a compound represented by Formula 2 below:

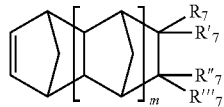

<Formula 2> wherein m is an integer of 0 to 4, $R_7$, $R'_7$, $R''_7$, and $R'''_7$ are each independently a polar functional group or a nonpolar functional group, and $R_7$, $R'_7$, $R''_7$, and $R'''_7$ may be connected to form a C4-C12 saturated or unsaturated cyclic group or a C6-C24 aromatic ring, wherein the nonpolar functional group is selected from the group consisting of hydrogen; halogen; C1-C20 straight or branched alkyl, haloalkyl, alkenyl, or haloalkenyl; C3-C20 straight or branched alkynyl or haloalkynyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; and C7-C15 aralkyl which is unsubstituted or substituted by alkyl, alkenyl, alkynyl, halogen, haloalkyl, haloalkenyl, or haloalkynyl, and wherein the polar functional group is a non-hydrocarbonaceous polar group comprising at least one of oxygen, nitrogen, phosphorus, sulfur, silicon, and boron, and is selected from the group consisting of:

—$R^8OR^9$, —$OR^9$, —$OC(O)OR^9$, —$R^8OC(O)OR^9$, —$C(O)R^9$, —$R^8C(O)R^9$, —$OC(O)R^9$, —$R^8C(O)OR^9$, —$C(O)OR^9$, —$R^8OC(O)R^9$, —$(R^8O)_k$—$OR^9$, —$(OR^8)_k$—$OR^9$, —$C(O)$—$O$—$C(O)R^9$, —$R^8C(O)$—$O$—$C(O)R^9$, —$SR^9$, —$R^8SR^9$, —$SSR^8$, —$R^8SSR^9$, —$S(=O)R^9$, —$R^8S(=O)R^9$, —$R^8C(=S)R^9$, —$R^8C(=S)SR^9$, —$R^8SO_3R^9$, —$SO_3R^9$, —$R^8N=C=S$, —$N=C=S$, —$NCO$, $R^8$—$NCO$, —$CN$, —$R^8CN$, —$NNC(=S)R^9$, —$R^8NNC(=S)R^9$, —$NO_2$, —$R^8NO_2$, —$P(R^9)_2$, —$R^8P(R^9)_2$, —$P(=O)(R^9)_2$, —$R^8P(=O)(R^9)_2$,

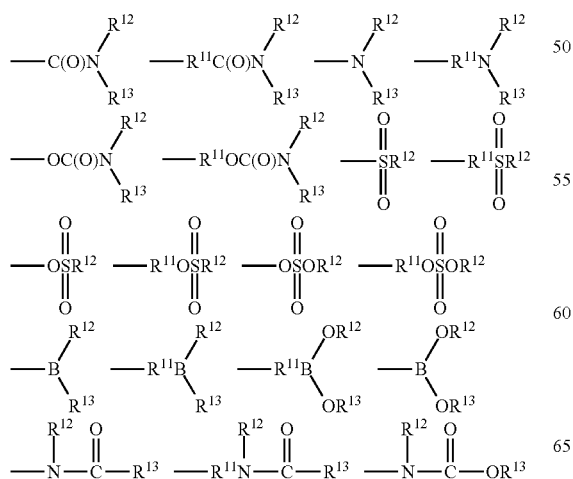

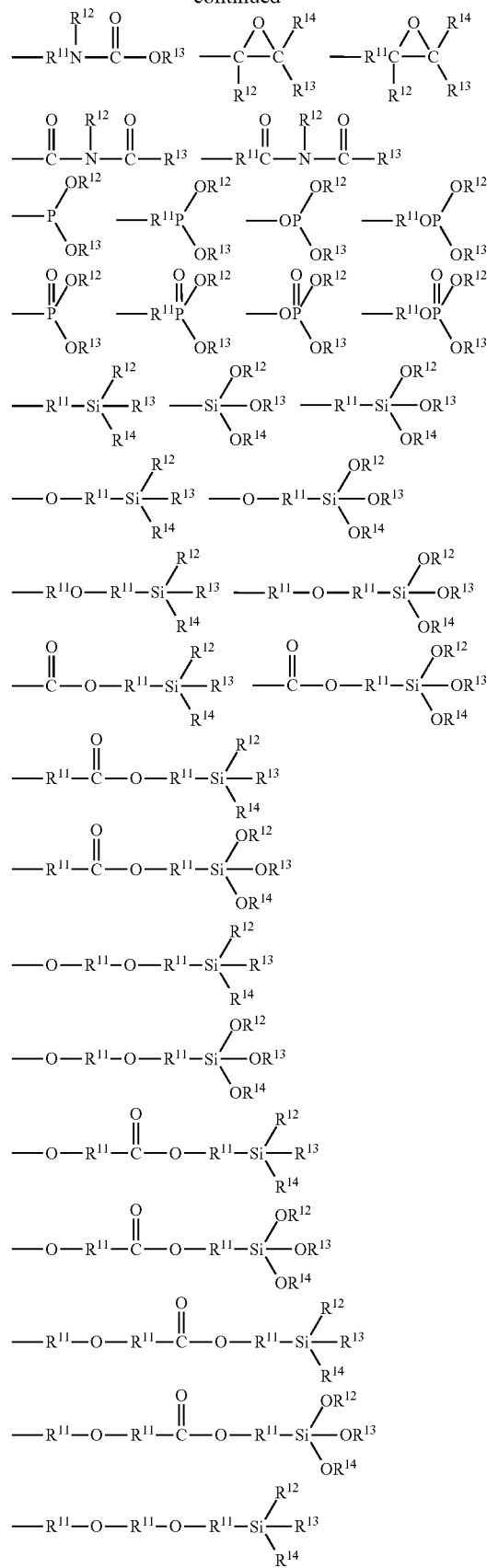

-continued

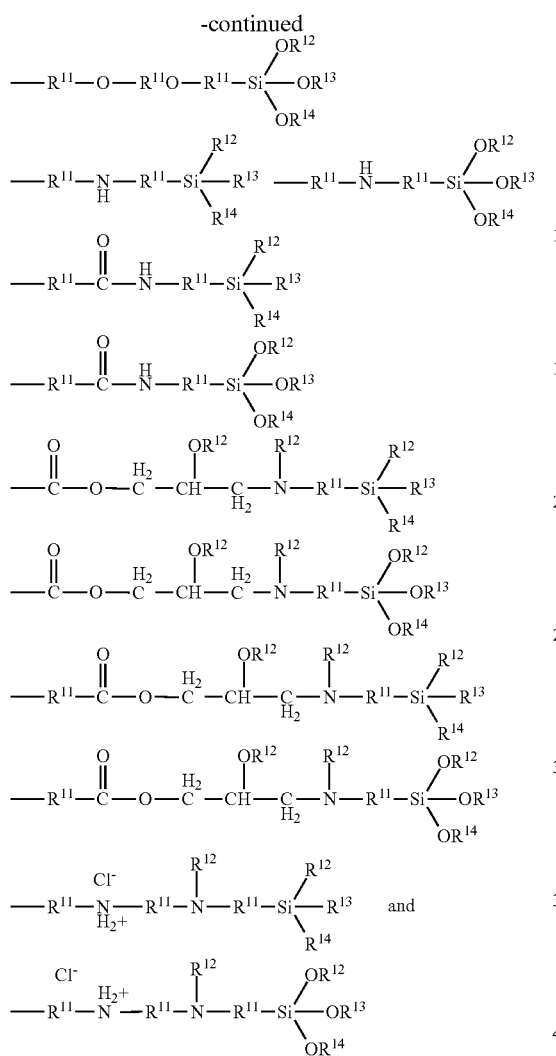

where $R^8$'s and $R^{11}$'s are each C1-C20 straight or branched alkylene, haloalkylene, alkenylene, or haloalkenylene; C3-C20 straight or branched alkynylene or haloalkynylene; C3-C12 cycloalkylene which is unsubstituted or substituted by alkyl, alkenyl, alkynyl, halogen, haloalkyl, haloalkenyl, or haloalkynyl; C6-C40 arylene which is unsubstituted or substituted by alkyl, alkenyl, alkynyl, halogen, haloalkyl, haloalkenyl, or haloalkynyl; or C7-C15 aralkylene which is unsubstituted or substituted by alkyl, alkenyl, alkynyl, halogen, haloalkyl, haloalkenyl, or haloalkynyl, $R^9$'s, $R^{12}$'s, $R^{13}$'s, and $R^{14}$'s are each hydrogen; halogen; C1-C20 straight or branched alkyl, haloalkyl, alkenyl, or haloalkenyl; C3-C20 straight or branched alkynyl or haloalkynyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or alkoxy, haloalkoxy, silyl, siloxy, aryloxy, haloaryloxy, carbonyloxy, or halocarbonyloxy, and k's are each an integer of 1 to 10.

3. The metal catalyst complex of claim 1, wherein the N-heterocyclic carbene ligand is at least one selected from the group consisting of compounds represented by Formulae 3A through 3D below:

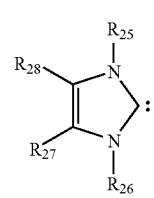

<Formula 3A>

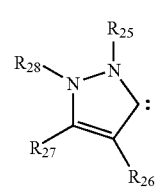

<Formula 3B>

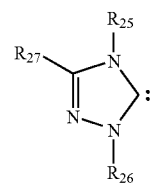

<Formula 3C>

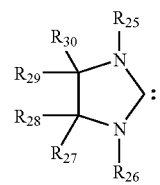

<Formula 3D> wherein $R_{25}$, $R_{26}$, $R_{27}$, $R_{28}$, $R_{29}$, and $R_{30}$ are each independently hydrogen, C1-C20 straight or branched alkyl, C3-C12 cycloalkyl, C2-C20 straight or branched alkenyl, C6-C15 cycloalkenyl, C3-C20 straight or branched allyl, C6-C30 aryl, C6-C30 heteroatom-containing aryl, or C7-C30 aralkyl, which may be substituted by at least one hydrocarbyl and/or heteroatom substituent selected from C1-C5 straight or branched alkyl, C1-C5 straight or branched haloalkyl, C2-C5 straight or branched alkenyl, C2-C5 straight or branched haloalkenyl, halogen, sulfur, oxygen, nitrogen, phosphorus, and a phenyl group which is unsubstituted or substituted by C1-C5 straight or branched alkyl, C1-C5 straight or branched haloalkyl, halogen, or a heteroatom.

4. The metal catalyst complex of claim 1, which is represented by Formula 5 below:

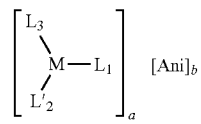

<Formula 5> wherein M, $L_1$, $L'_2$, $L_3$, [Ani], a, and b are as defined in claim 1.

5. The metal catalyst complex of claim 1, which is selected from compounds represented by Formulae 6A through 6D below:

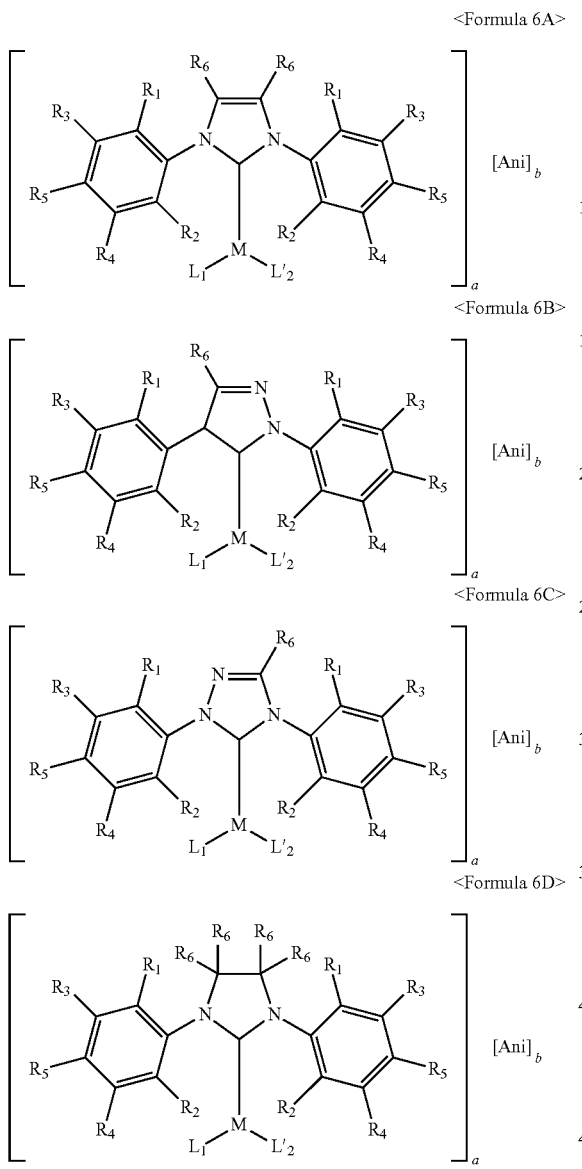

<Formula 6A>

<Formula 6B>

<Formula 6C>

<Formula 6D> wherein M, $L_1$, $L'_2$, [Ani], a, and b are as defined in claim 1, $R_1$ through $R_6$ are each independently hydrogen; halogen; C1-C20 straight or branched alkyl, alkoxy, alkenyl or vinyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or C3-C20 alkynyl, and at least one of $R_1$ through $R_6$ is halogen or a halogen-containing alkyl, aryl, aralkyl, or alkylaryl group.

6. The metal catalyst complex of claim 1, which is represented by Formula 7 below:

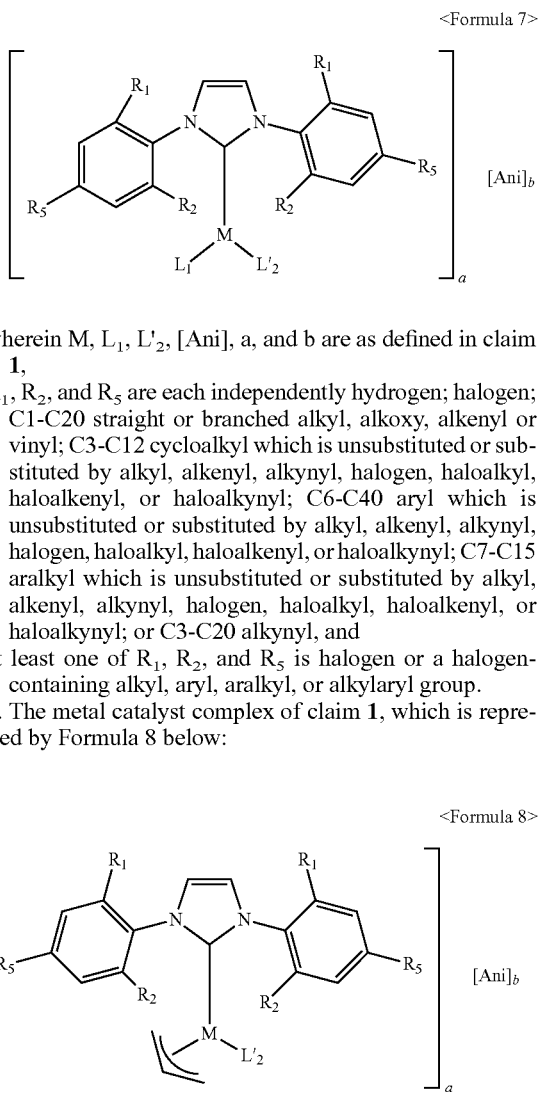

<Formula 7> wherein M, $L_1$, $L'_2$, [Ani], a, and b are as defined in claim 1, $R_1$, $R_2$, and $R_5$ are each independently hydrogen; halogen; C1-C20 straight or branched alkyl, alkoxy, alkenyl or vinyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or C3-C20 alkynyl, and at least one of $R_1$, $R_2$, and $R_5$ is halogen or a halogen-containing alkyl, aryl, aralkyl, or alkylaryl group.

7. The metal catalyst complex of claim 1, which is represented by Formula 8 below:

<Formula 8> wherein M, $L'_2$, [Ani], a, and b are as defined in claim 1, $R_1$, $R_2$, and $R_5$ are each independently hydrogen; halogen; C1-C20 straight or branched alkyl, alkoxy, alkenyl or vinyl; C3-C12 cycloalkyl which is unsubstituted or substituted by alkyl, alkenyl, alkynyl, halogen, haloalkyl, haloalkenyl, or haloalkynyl; C6-C40 aryl which is unsubstituted or substituted by alkyl, alkenyl, alkynyl, halogen, haloalkyl, haloalkenyl, or haloalkynyl; C7-C15 aralkyl which is unsubstituted or substituted by alkyl, alkenyl, alkynyl, halogen, haloalkyl, haloalkenyl, or haloalkynyl; or C3-C20 alkynyl, is C3 allyl, and at least one of $R_1$, $R_2$, and $R_5$ is halogen or a halogen-containing alkyl, aryl, aralkyl, or alkylaryl group.

* * * * *